(12) United States Patent
Bagnod et al.

(10) Patent No.: US 8,926,955 B2
(45) Date of Patent: Jan. 6, 2015

(54) SYNTHESIS OF POLYMER CONJUGATES OF INDOLOCARBAZOLE COMPOUNDS

(75) Inventors: Raffaella Bagnod, Turin (IT); Luca Beccaria, Turin (IT); Luisa Bertarione Rava Rossa, Turin (IT); Domenico Criscuolo, Milan (IT); Chiara Lorenzetto, Turin (IT); Valentina Mainero, Turin (IT); Alessandra Marconi, Reggio Emilia (IT); Carlo Pincelli, Modena (IT); Silvio Traversa, Turin (IT)

(73) Assignee: Creabilis S.A., Luxembourg (LU)

( * ) Notice: Subject to any disclaimer, the term of this patent is extended or adjusted under 35 U.S.C. 154(b) by 797 days.

(21) Appl. No.: 13/141,354

(22) PCT Filed: Dec. 22, 2009

(86) PCT No.: PCT/EP2009/067817
§ 371 (c)(1),
(2), (4) Date: Sep. 9, 2011

(87) PCT Pub. No.: WO2010/072795
PCT Pub. Date: Jul. 1, 2010

(65) Prior Publication Data
US 2011/0311451 A1  Dec. 22, 2011

Related U.S. Application Data

(60) Provisional application No. 61/152,055, filed on Feb. 12, 2009, provisional application No. 61/139,816, filed on Dec. 22, 2008.

(51) Int. Cl.
*A61K 47/48* (2006.01)
(52) U.S. Cl.
CPC ............................... *A61K 47/48215* (2013.01)
USPC .................................... 424/78.17; 424/78.37
(58) Field of Classification Search
None
See application file for complete search history.

(56) References Cited

U.S. PATENT DOCUMENTS 5,516,772 A   5/1996   Glicksman et al.

FOREIGN PATENT DOCUMENTS

| WO | 91/05545 A1 | 5/1991 |
| WO | 91/05546 A1 | 5/1991 |
| WO | 93/24476 A1 | 12/1993 |
| WO | 94/21235 A1 | 9/1994 |
| WO | 95/07911 A1 | 3/1995 |
| WO | 2007022999 A1 | 3/2007 |

OTHER PUBLICATIONS

Translation of Notification of Reasons for Refusal in the corresponding Japanese Patent Application No. 2011-542820 dated Sep. 24, 2013, 6 pgs.
Mashkovsky, "Novaya Volna", Drugs, 2001, vol. 1, p. 11, Translation only.
English translation of an office action issued on Mar. 21, 2013 in corresponding Russian application No. 2011130512 (3 pgs.).
Schneider et al., "Increasing the Kinase Specificity of K252a by Protein Surface Recognition", Organic Letters, 2005, vol. 7, No. 9, pp. 1695-1968.
Veronese et al., "PEGylation, successful approach to drug delivery", Drug Discovery Today, vol. 10, No. 21, Nov. 2005, pp. 1451-1458.
Annex 1 to EPO form 2300E, Opposition by Bl03 Research S.R.L. to the grant of European Patent No. EP1919979 B1 in the name of CREABILIS THERAPEUTICS S.P.A., Facts and Arguments (Rule 76(2)(c) EPC), dated Oct. 10, 2014, 5 pgs.

*Primary Examiner* — James Rogers
(74) *Attorney, Agent, or Firm* — Rothwell, Figg, Ernst & Manbeck, P.C.

(57) ABSTRACT

The present invention relates to a process for the preparation of polymer conjugates of indolocarbaxole compounds, in particular of polymer conjugates of K-252a and derivatives thereof, by a synthetic route which results in a highly pure product, with a high product yield. In a further aspect the present invention relates to novel polymer conjugates of K-252a and derivatives thereof, wherein the chemical group linking the polymer unity to the K-252a or to the K-252a derivative compound is characterized by a 5-member oxazolidindionic cyclic structure. These novel polymer conjugates are obtained through the novel synthetic route with high purity and high yields.

37 Claims, 13 Drawing Sheets

Figure 2 (continued)

```
Current Data Parameters
NAME        p08508_CT327_mPEG_NHCOIm_14_05_08
EXPNO                        1
PROCNO                       1

F2 - Acquisition Parameters
Date_              20080514
Time                  16.31
INSTRUM               spect
PROBHD        5 mm BBI 1H-BB
PULPROG                  zg
TD                    35918
SOLVENT                DMSO
NS                       32
DS                        2
SWH              7183.908 Hz
FIDRES          0.200009 Hz
AQ            2.4999428 sec
RG                     45.3
DW                69.600 usec
DE                 6.00 usec
TE                  300.0 K
D1          5.00000000 sec
TD0                       1
```

Figure 2 (continued)

```
======== CHANNEL f1 ========
NUC1                 1H
P1              3.00 usec
PL1            -1.00 dB
SFO1      400.1315764 MHz F2 - Processing parameters
SI              32768
SF        400.1300000 MHz
WDW                EM
SSB                 0
LB               0.30 Hz
GB                  0
PC               1.00
```

Figure 4 (continued)

```
Current Data Parameters
NAME        p06208_CT327_IA25B1
EXPNO                        3
PROCNO                       1

F2 - Acquisition Parameters
Date_               20080407
Time                    9.09
INSTRUM                spect
PROBHD     5 mm BBI 1H-BB
PULPROG                   zg
TD                     35918
SOLVENT                 DMSO
NS                        64
DS                         2
SWH             7183.908 Hz
FIDRES         0.200009 Hz
AQ            2.4999428 sec
RG                      25.4
DW               69.600 usec
DE                6.00 usec
TE                  300.0 K
D1           5.00000000 sec
TD0                        1
```

Figure 4 (continued)

```
======== CHANNEL f1 ========
NUC1                 1H
P1              3.00 usec
PL1            -1.00 dB
SFO1      400.1315764 MHz F2 - Processing parameters
SI              32768
SF        400.1300000 MHz
WDW                EM
SSB                 0
LB               0.30 Hz
GB                  0
PC               1.00
```

Figure 5 (continued)

```
Current Data Parameters
NAME         p06208_CT327_IA25B1
EXPNO                          2
PROCNO                         1

F2 - Acquisition Parameters
Date_                   20080405
Time                       12.47
INSTRUM                    spect
PROBHD      5 mm BBI 1H-BB
PULPROG                     zgpg
TD                         50922
SOLVENT                     DMSO
NS                         16384
DS                             4
SWH                 24154.590 Hz
FIDRES               0.474345 Hz
AQ                 1.0541354 sec
RG                         16384
DW                   20.700 usec
DE                    30.00 usec
TE                       300.0 K
D1                3.00000000 sec
d11               0.03000000 sec
DELTA             2.90000010 sec
TD0                            1
```

Figure 5 (continued)

```
======== CHANNEL f1 ========
NUC1                13C
P1             10.00 usec
PL1            -6.00 dB
SFO1      100.6238364 MHz ======== CHANNEL f2 ========
CPDPRG2          waltz16
NUC2                 1H
PCPD2          80.00 usec
PL2            -1.00 dB
PL12           16.20 dB
PL13           19.00 dB
SFO2      400.1322007 MHz F2 - Processing parameters
SI              131072
SF         100.6127690 MHz
WDW                 EM
SSB                  0
LB                3.30 Hz
GB                   0
PC                1.40
```

SYNTHESIS OF POLYMER CONJUGATES OF INDOLOCARBAZOLE COMPOUNDS

CROSS REFERENCE TO RELATED APPLICATION

This application is a 35 U.S.C. 371 National Phase Entry Application from PCT/EP2009/067817, filed Dec. 22, 2009, which claims the benefit of U.S. Provisional Application No. 61/139,816 filed on Dec. 22, 2008 and U.S. Provisional Application No. 61/152,055 filed on Feb. 12, 2009, the disclosures of which are incorporated herein in their entirety by reference.

The present invention relates to a process for the preparation of polymer conjugates of indolocarbazole compounds, in particular of polymer conjugates of K-252a and derivatives thereof, by a synthetic route which results in a highly pure product, with a high product yield.

In a further aspect the present invention relates to novel polymer conjugates of K-252a and derivatives thereof, wherein the chemical group linking the polymer unity to the K-252a compound or to the K-252a derivative compound is characterised by a 5-member oxazolidindionic cyclic structure. These novel polymer conjugates are obtained through the novel synthetic route with high purity and high yields.

In literature the therapeutic potential of K-252a and derivatives thereof in the prevention, alleviation and treatment of kinase-associated pathologies, in particular of HMGB1-associated pathologies such as neurological disorders, neuropathies and neurodegenerative disorders of the central and peripheral nervous system is described (for example from PCT/EP2005/008258, Annu Rev Pharmacol Toxicol. 2004; 44:451-74; Neurochem Int. 2001 November-December; 39(5-6):459-68; Neuroport. 2000 Nov. 9; 11(16):3453-6; Neuroscience. 1998 September; 86(2):461-72; Brains Res. 1994 Jul. 4; 650(1):170-4). Moreover, the state of the art discloses the therapeutic effectiveness of these indolocarbazole compounds in the prevention, alleviation and treatment of dermal pathologies, in particular dermal pathologies associated with an excessive keratinocyte proliferation, such as psoriasis (for example from WO 2005/014003, Raychaudhuri et al., J. Invest. Dermatol. 122:812-819, 2004). Still further it was reported in the art that K-252a and its derivatives are useful as active agents against NGF-related pain (for example from Koizumi et al., J. Neurosci. 8:715-721, 1988; Doherty et al., Neurosci. Lett. 96:1-6, 1989; Matsuda et al., Neurosci. Lett. 87:11-17, 1988, Winston J H et al. J. Pain (2003) 4:329-337). Hence, the biological importance and therapeutic activity of the indolocarbazole compound K-252a and its derivatives are well reported in literature (for example from Kim et al., Biol. Pharm. Bull. 21:498-505, 1998, Schneider et al., Org. Lett. 7:1695-1698, 2005).

Polymer conjugates of K-252a and derivatives thereof and their use as active agents in pharmaceutical compositions useful for the prevention, alleviation and treatment of pathologies as described above are disclosed in WO 2007/022999. The disclosure of said application is herein incorporated by reference. According to WO 2007/022999 the aim of conjugating to a polymer and in particular of pegylating the active K-252a indolocarbazole derivative compounds, is to develop administration forms of said active compounds which permit an improved pharmacokinetic and toxicologic performance, achieving the best bioavailability of K-252a or of its derivative in the various possible application routes.

The synthetic approach described in WO 2007/022999 for the production of the polymer conjugates of K-252a and its derivatives includes a covalent attachment of the polymer moiety to the indolocarbazole structure of the K-252a compound or its derivatives. In particular WO 2007/022999 discloses the reaction of an isocyanate-activated polymer with an hydroxyl group on the C3 position of the tetrahydrofuran moiety of the K-252a or its derivative under suitable reaction conditions, whereby a carbamide bond is obtained as covalent linkage between the polymer moiety and the active compound.

Since polymer conjugates of K-252a and derivatives thereof with a high purity are highly needed for medical application, it was the object of the present invention to provide a method for the production of polymer conjugates of the active indolocarbazole compounds, which results in a highly pure reaction product, obtained in high and consistent yields. Moreover, the aim of the invention was further to eliminate complex purification steps and to permit an easy purification and recovery of the target polymer conjugated compound, in order to maximise the efficiency of the polymer conjugation reaction.

Surprisingly, the inventors found that reacting the K-252a or derivative compound with a ω-1-H-imidazole-carboxamide polymer moiety used as starting polymer reagent of the conjugation reaction provided a controlled conjugation process, thus obtaining a desired higher yield and purity of the resulting indolocarbazole-polymer conjugate.

Hence, the present invention relates to a process for the preparation of a polymer conjugate of an indolocarbazole compound of formula (I)

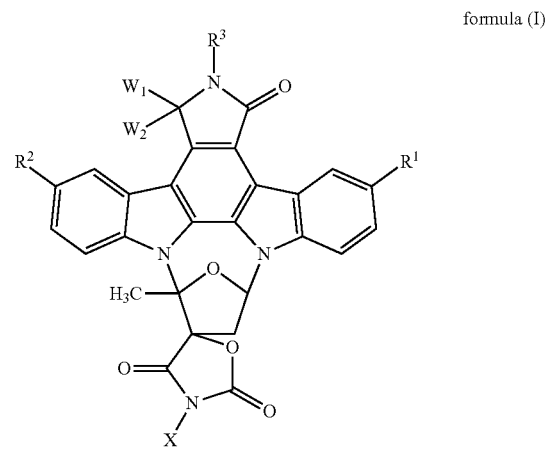

formula (I)

wherein
$R^1$ and $R^2$ are the same or a different residue and are each independently selected from the group consisting of:
(a) hydrogen, halogen, substituted or unsubstituted lower alkyl, substituted or unsubstituted lower alkenyl, substituted or unsubstituted lower alkynyl, hydroxy, lower alkoxy, carboxy, lower alcoxycarbonyl, acyl, nitro, carbamoyl, lower alkylaminocarbonyl, —$NR^5R^6$, wherein $R^5$ and $R^6$ are each independently selected from hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, substituted or unsubstituted aralkyl, substituted or unsubstituted lower alkylaminocarbonyl, substituted or unsubstituted arylaminocarbonyl, alkoxycarbonyl, carbamoyl, acyl or $R^5$ and $R^6$ are combined with a nitrogen atom to form a heterocyclic group, (b) —CO(CH$_2$)$_j$R$^4$, wherein j is 1 to 6, and R$^4$ is selected from the group consisting of
  (i) hydrogen, halogen, —N$_3$,
  (ii) —NR$^5$R$^6$, wherein R$^5$ and R$^6$ are as defined above,
  (iii) —SR$^7$, wherein R$^7$ is selected from the group consisting of hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, substituted or unsubstituted aralkyl, —(CH$_2$)$_a$CO$_2$R$^{10}$ (wherein a is 1 or 2, and wherein R$^{10}$ is selected from the group consisting of hydrogen and substituted or unsubstituted lower alkyl) and —(CH$_2$)$_a$CO$_2$NR$^5$R$^6$,
  (iv) —OR$^8$, —OCOR$^8$, wherein R8 is selected from hydrogen, substituted or unsubstituted lower alkyl, substituted or unsubstituted lower alkenyl, substituted or unsubstituted lower alkynyl, substituted or unsubstituted aryl, substituted or unsubstituted heteroaryl
(c) —CH(OH)(CH$_2$)$_j$R$^{4"}$ wherein j and R$^4$ are as defined above;
(d) —(CH$_2$)$_d$CHR$^{11}$CO$_2$R$^{12}$ or —(CH$_2$)$_d$CHR$^{11}$CONR$^5$R$^6$, wherein d is 0 to 5, R$^{11}$ is hydrogen, —CONR$^5$R$^6$, or —CO$_2$R$^{13}$, wherein R$^{13}$ is hydrogen or a wherein substituted or unsubstituted lower alkyl, and R$^{12}$ is hydrogen or a substituted or unsubstituted lower alkyl;
(e) —(CH$_2$)$_k$R$^{14}$ wherein k is 2 to 6 and R$^{14}$ is halogen, substituted or unsubstituted aryl, substituted or unsubstituted heteroaryl, —COOR$^{15}$, —OR$^{15}$, (wherein R$^{15}$ is hydrogen, substituted or unsubstituted lower alkyl, substituted or unsubstituted lower alkenyl, substituted or unsubstituted lower alkynyl, substituted or unsubstituted aryl, substituted or unsubstituted heteroaryl or acyl), —SR$^7$ (wherein R$^7$ is as defined above), —CONR$^5$R$^6$, —NR$^5$R$^6$ (wherein R$^5$ and R$^6$ are as defined above) or —N$_3$;
(f) —CH=CH(CH$_2$)$_m$R$^{16}$, wherein m is 0 to 4, and R$^{16}$ is hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, —COOR$^{15}$, —OR$^{15}$ (wherein R$^{15}$ is as defined above) —CONR$^5$R$^6$ or —NR$^5$R$^6$ (wherein R$^5$ and R$^6$ are as defined above);
(g) —CH=C(CO$_2$R$^{12}$)$_2$, wherein R$^{12}$ is as defined above;
(h) —C≡C(CH$_2$)$_n$R$^{16}$, wherein n is 0 to 4 and R$^{16}$ is as defined above;
(i) —CH$_2$OR$^{22}$, wherein R$^{22}$ is tri-lower alkyl silyl in which the three lower alkyl groups are the same or different or wherein R$^{22}$ has the same meaning as R$^8$.
(j) —CH(SR$^{23}$)$_2$ and —CH$_2$—SR$^7$ wherein R$^{23}$ is lower alkyl, lower alkenyl or lower alkynyl and wherein R$^7$ is as defined above; and
R$_3$ is hydrogen, halogen, acyl, carbamoyl, substituted or unsubstituted lower alkyl, substituted or unsubstituted alkenyl, substituted or unsubstituted lower alkynyl or amino; and
W$^1$ and W$^2$ are independently hydrogen, hydroxy or W$^1$ and W$^2$ together represent oxygen;
and wherein X is a polymer moiety,
whereby the process comprises reacting a ω-1H-imidazole-carboxamide polymer compound of general formula (II)

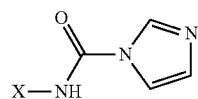
formula (II)

wherein X is defined as above,
with an indolocarbazole compound of general formula (III)

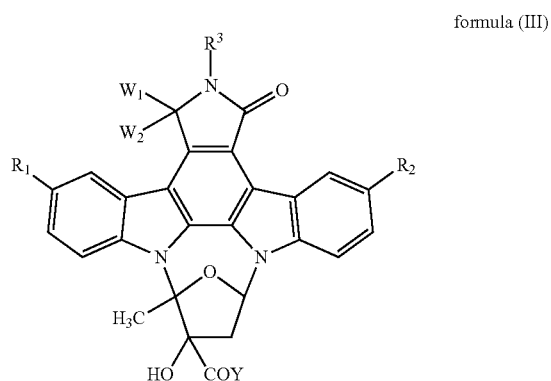
formula (III)

wherein R$_1$, R$_2$, R$_3$, W$_1$ and W$_2$ are defined as above and which are optionally protected by protecting groups and wherein Y represents a leaving group, and wherein the process further optionally comprises deprotecting the protecting groups from the optionally protected R$_1$, R$_2$, R$_3$, W$_1$ and W$_2$ in order to obtain the compound of formula (I).

The conjugation reaction of the process of the invention to synthesize the conjugate polymer compound of formula (I) is catalysed by a base in an organic solvent. Preferably the base is a strong base. In a preferred embodiment of the present invention, the base is selected from the group of alkali metal hydrides, tertiary amines and/or alkoxide. In a very preferred embodiment of the present invention, the base catalysing the polymer conjugation reaction of the invention is sodium hydride. Other bases, such as sodium methoxide, or triethylamine can also be used, however.

The molar ratio of the base catalyst to the compound of formula (III) is preferably between about 1:1 and about 4:1, most preferably about 1:1 to about 1.5:1 and most preferably about 1:1.

Furthermore, the reaction of the invention is carried out in an organic solvent, preferably in anhydrous conditions, i.e. in a dry organic solvent. Preferably, the water content in the solution mixture of the conjugation process is equal or less than 200 ppm. The organic solvent may be selected from the group of dichloromethane, chloroform, N,N-dimethylformamide. In a very preferred embodiment of the present invention, the organic solvent is dichloromethane, even more preferably anhydrous dichloromethane.

It is further preferred according to the invention that the conjugation reaction is carried out under inert gas atmosphere, such as nitrogen or argon atmosphere.

Moreover, the reaction of the process of the invention is preferably carried out at a temperature of about −10° to about 60° C., more preferably of about 0° to about 25° C. and most preferably at room temperature after an initial step at 0° C.

Following the production of the target compound of formula (I) according to the process of the invention, the polymer conjugate of formula (I) may then be separated and purified from the reaction mixture. According to a preferred embodiment of the invention the compound of formula (I) is obtained by purification of the crude mixture by flash chromatography. An automated gradient flash purification system is preferably used and is equipped with a suitable column and solvent. The purification method is preferably selected from reverse phase and direct phase columns and the conditioning/elution solvent is preferably selected from dichloromethane, water, methanol, acetonitrile, ammonium formate buffer solution at different mixture ratios. In a very preferred embodiment of the invention the indolocarbazole-polymer compound of formula (I) is purified by a reverse phase flash chromatography equipped with a C18 cartridge and the purification is carried out by isocratic elution with acetonitrile/5 mM ammonium formate buffer (pH 3.5) 40:60 (as reported in Example 3). In a further preferred embodiment of the invention, the indolocarbazole-polymer compound of formula (I) is purified by a normal phase flash chromatography (as described in the Examples 4 and 5.3).

The product may then be dried e.g. over sodium sulphate and filtered off and the solvent is removed by evaporation under reduced pressure at 25° C. Purification of the target product is carried out by common techniques known by the person skilled in the art.

After the purification step the resultant polymer compound of formula (I) has a purity of at least about 95%. More preferably after the purification step the compound of formula (I) has a purity of at least about 98%. In an even more preferred embodiment the resultant polymer compound has a purity of 98.5%, 99% or even 99.5%.

Moreover, the process of the present invention results in an overall mass yield of the compound of formula (I) from about 40% to about 98% by weight, preferably from about 50% to about 95% by weight based on the weight of the reactant compound of formula (III).

The residue Y of formula (III) is a leaving group, i.e. a group which under the reaction conditions of the polymer conjugation of the invention is detached from the structure of the compound of formula (III) in order to obtain the oxazolidindionic cycle of the compound of formula (I), which covalently links the polymer moiety to the indolocarbazole structure of the K-252a or its derivative compound. According to the invention, also the imidazole ring of the compound of general formula (II) is detached during the conjugation reaction from the polymer reactant moiety in order to obtain the compound of formula (I).

In a preferred embodiment of the present invention, the leaving group Y of formula (III) is selected from the group including a triflate, a tosylate, a mesylate, a sulfate, a halogen, a hydroxy or a lower alkoxy group. In an especially preferred embodiment, the leaving group Y of formula (III) is a lower alkoxy group or a hydroxy group. Most preferably, the leaving group Y is a lower alkoxy group, in particular a methoxy group.

The polymer moiety which is covalently attached to the indolocarbazole compound with the process of the present invention and which is, for example, represented in the general formulae (I) and (II) by X, has to be biocompatible, can be of natural or semi-synthetic or synthetic origin and can have a linear or branched structure. Preferably, the polymer X in the present invention is selected from poly(alkylene oxides), in particular from (polyethylene) oxides. However, further exemplary polymers include without limitation polyacrylic acid, polyacrylates, polyacrylamide or N-alkyl derivatives thereof, polymethacrylic acid, polymethacrylates, polyethylacrylic acid, polyethylacrylates, polyvinylpyrrolidone, poly(vinylalcohol), polyglycolic acid, polylactic acid, poly(lactic-co-glycolic) acid, dextran, chitosan, polyaminoacids, hydroxyethyl starch.

In order to participate to the process of the present invention, in particular in order to be functionalized to the reactant polymer of formula (II) of the process of the invention, the above-mentioned polymer moiety should carry an amino functional end-group or should be functionalized to carry an amino functional end-group. Hence, the polymer moiety should be an amino-activated polymer of general formula X—NH$_2$.

In fact, the starting polymer reactant of formula (II) is obtained by reaction of the amino group of a polymer moiety with a 1,1-carbonyldiimidazole compound to obtain a ω-1H-imidazole-carboxamide polymer compound of general formula (II).

The formation of the ω-1H-imidazole-carboxamide polymer compound of formula (II) is preferably carried out in an organic solvent such as dichloromethane, chloroform, N,N-dimethylformamide. In a very preferred embodiment, the organic solvent is dichloromethane, even more preferably anhydrous dichloromethane.

It is further preferred according to the invention, that the activation of the ω-amino polymer is carried out under inert gas atmosphere, such as nitrogen or argon atmosphere.

Moreover, the reaction of formation of the ω-1H imidazole carboxamide polymer compound of the invention is preferably carried out at a temperature of about 10° to about 60° C., more preferably of about 15° to about 25° C. and most preferably at room temperature.

In a very preferred embodiment of the present invention, the polymer moiety X is a polyethylene glycol (PEG) moiety, wherein the terminal OH group can optionally be modified e.g. with $C_1$-$C_5$ alkyl or $C_1$-$C_5$ acyl groups, preferably with $C_1$-, $C_2$- or $C_3$-alkyl groups or $C_1$-, $C_2$- or $C_3$ groups. Preferably, the modified polyethylene glycol is a terminally alkoxy-substituted polyethylene glycol, more preferably a methoxy-polyethylene-glycol (mPEG).

The polymer used according to the present invention has a molecular weight ranking from about 100 to about 100,000 Da, preferably from about 200 to about 50,000 Da, and more preferably from about 500 to about 10,000 Da. According to one preferred aspect of the invention, the polymer is a short-chain poly(ethylene glycol), preferably a terminally alkoxy-substituted PEG, such as a methoxy-substituted poly(ethylene glycol) with a molecular weight ranking from about 200 to about 1500 Da, preferably from about 400 to about 1200 Da and even more preferably from about 550 to about 1100. In the most preferred embodiment, the short-chain PEG or mPEG has an average molecular weight of about 550 Da or of about 1100 Da. According to a second preferred aspect of the invention, the polymer is a long-chain poly(ethylene glycol), preferably a terminally alkoxy-substituted PEG, such as methoxy-substituted poly(ethylene glycol), with a molecular weight ranking from about 4,000 to about 6,000 Da, and preferably from about 4,500 to about 5,500 Da. In the most preferred embodiment of this aspect of the invention, the long-chain PEG or mPEG has an average molecular weight of about 2,000 Da or of about 5,000 Da.

The term "about" as used above to define the values and ranges of molecular weights of the polymer moiety of the invention means that the indicated values and/or range limits can vary within ±20%, preferably within ±10%.

As used in this application, except as otherwise expressly provided herein, each of the following terms shall have the meaning set forth below.

The term "lower alkyl", when used alone or in combination with other groups, means a straight chained or branched lower alkyl group containing from 1-6 carbon atoms, preferably from 1-5, more preferably from 1-4 and especially preferably 1-3 or 1-2 carbon atoms. These groups include in particular methyl, ethyl, propyl, isopropyl, butyl, isobutyl, sec-butyl, tert-butyl, pentyl, amyl, isoamyl, neopentyl, 1-ethylpropyl, hexyl, and the like. The lower alkyl moiety of the "lower alkoxy", the "lower alkoxycarbonyl", the "lower alkylaminocarbonyl", "lower hydroxyalkyl" and of the "tri-lower alkylsilyl" groups has the same meaning as "lower alkyl" defined above.

The "lower alkenyl" groups are defined as $C_2$-$C_6$ alkenyl groups which may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1, 3 or 2,4-pentadienyl, and the like. More preferred $C_2$-$C_6$-alkenyl groups are $C_2$-$C_5$-, $C_2$-$C_4$-alkenyl groups and even more preferably $C_2$-$C_3$-alkenyl groups.

The term "lower alkynyl" groups refers to $C_2$-$C_6$-alkynyl groups which may be straight chained or branched and include ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. More preferred $C_2$-$C_6$-alkynyl groups are $C_2$-$C_5$-, $C_2$-$C_4$-alkynyl groups and even more preferably $C_2$-$C_3$-alkynyl groups.

The term "aryl" group refers to $C_6$-$C_{14}$-aryl groups which contain from 6 up to 14 ring carbon atoms. These groups may be mono-, bi- or tricyclic and are fused rings. The preferred aryl groups include phenyl, biphenyl, naphthyl, anthracenyl, phenanthrenyl and the like. The aryl moiety of the "arylcarbonyl" and the "arylaminocarbonyl" groups has the same meaning as defined above.

The term "heteroaryl" groups may contain 1 to 3 heteroatoms independently selected from nitrogen, sulfur or oxygen and refers $C_3$-$C_{13}$-heteroaryl groups. These groups may be mono-, bi- or tricyclic. The $C_3$-$C_{13}$ heteroaryl groups of the present invention include heteroaromatics and saturated and partially saturated heterocyclic groups. These heterocyclics may be monocyclic, bicyclic, tricyclic. Preferred 5 or 6-membered heterocyclic groups are thienyl, furyl, pyrrolyl, pyridyl, pyranyl, morpholinyl, pyrazinyl, methylpyrrolyl, and pyridazinyl. The $C_3$-$C_{13}$-heteroaryl may be a bicyclic heterocyclic group. Preferred bicyclic heterocyclic groups are benzofuryl, benzothienyl, indolyl, imidazolyl, and pyrimidinyl. The most preferred $C_3$-$C_{13}$-heteroaryls are furyl and pyridyl.

The term "lower alkoxy" includes alkoxy groups containing from 1 to 6 carbon atoms, preferably from 1 to 5, more preferably from 1-4 and especially preferably 1 to 3 or 1 to 2 carbon atoms and may be straight chained or branched. These groups include methoxy, ethoxy, propoxy, butoxy, isopropoxy, tert-butoxy, pentoxy, hexoxy and the like.

The term "acyl" includes lower alkanoyl containing 1 to 6 carbon atoms, preferably from 1 to 5, from 1 to 4, from 1 to 3 or from 1 to 2 carbon atoms and may be straight chained or branched. These groups include preferably formyl, acetyl, propionyl, butyryl, isobutyryl, tertiary butyryl, pentanoyl and hexanoyl. The acyl moiety of the "acyloxy" group has the same meaning as defined above.

The term "halogen" includes fluoro, chloro, bromo, iodio, and the like.

The term "aralkyl" group refers $C_7$-$C_{15}$-aralkyl wherein the alkyl group is substituted by an aryl. The alkyl group and aryl may be selected from the $C_1$-$C_6$ alkyl groups and the $C_6$-$C_{14}$-aryl groups as defined above, wherein the total number of carbon atoms is between 7 and 15. Preferred $C_7$-$C_{15}$-aralkyl groups are benzyl, phenylethyl, phenylpropyl, phenylisopropyl, phenylbutyl, diphenylmethyl, 1,1-diphenylethyl, 1,2-diphenylethyl. The aralkyl moiety of the "aralkyloxy" groups has the same meaning as defined above.

The substituted lower alkyl, alkenyl and alkynyl groups have 1 to 3 independently selected substituents, such as lower alkyl, hydroxy, lower alkoxy, carboxyl, lower alkoxycarbonyl, nitro, halogen, amino, mono- or di-lower alkylamino, dioxolane, dioxane, dithiolane, and dithione. The lower alkyl substituent moiety of the substituted lower alkyl, alkenyl and alkynyl groups, and the lower alkyl moiety of the lower alkoxy, the lower alkoxycarbonyl, and the mono- or di-lower alkylamino substituents of the substituted lower alkyl, alkenyl and alkynyl groups have the same meaning as "lower alkyl" defined above.

The substituted aryl, the substituted heteroaryl and the substituted aralkyl groups each has 1 to 3 independently selected substituents, such as lower alkyl, hydroxy, lower alkoxy, carboxy, lower alkoxycarbonyl, nitro, amino, mono- or di-lower alkylamino, and halogen. The lower alkyl moiety of the lower alkyl, the lower alkoxy, the lower alkoxycarbonyl, and the mono- or di-lower alkylamino groups among the substituents has the same meaning as lower alkyl defined above.

The heterocyclic group formed by $R^5$ and $R^6$ combined with a nitrogen atom includes pyrrolidinyl, piperidinyl, piperidino, morpholinyl, morpholino, thiomorpholino, N-methylpiperazinyl, indolyl, and isoindolyl.

Preferably, $R^1$ and $R^2$ are independently selected from the group consisting of hydrogen, halogen, nitro, —$CH_2OH$, —$(CH_2)_kR^{14}$, —CH=CH$(CH_2)_mR^{16}$, —C≡C$(CH_2)_nR^{15}$, —CO$(CH_2)_jR^4$ wherein $R^4$ is —$SR^7$, $CH_2$O-(substituted or unsubstituted) lower alkyl (wherein the substituted lower alkyl is preferably methoxymethyl, methoxyethyl or ethoxymethyl), —$NR^5R^6$.

In the above preferred meanings of $R^1$ and $R^2$, the residue $R^{14}$ is preferably selected from phenyl, pyridyl, imidazolyl, thiazolyl, tetrazolyl, —COOR$^{15}$, —OR$^{15}$ (wherein $R^{15}$ is preferably selected from hydrogen, methyl, ethyl, phenyl or acyl), —$SR^7$ (wherein $R^7$ is preferably selected from substituted or unsubstituted lower alkyl, 2-thiazoline and pyridyl) and —$NR^5R^6$ (wherein $R^5$ and $R^6$ are preferably selected from hydrogen, methyl, ethyl, phenyl, carbamoyl and lower alkylaminocarbonyl). Moreover the residue $R^{16}$ is preferably selected from hydrogen, methyl, ethyl, phenyl, imidazole, thiazole, tetrazole, —COOR$^{15}$, —OR$^{15}$ and —$NR^5R^6$ (wherein the residues $R^{15}$, $R^5$ and $R^6$ have the preferred meanings as described above). In the above preferred meanings of $R^1$ and $R^2$, the residue $R^7$ is preferably selected from the group consisting of substituted or unsubstituted lower alkyl, substituted or unsubstituted phenyl, pyridyl, pyrimidinyl, thiazole and tetrazole. Further k is preferably 2, 3 or 4, j is preferably 1 or 2 and m and n are independently preferably 0 or 1.

Preferably $R^3$ is hydrogen or acetyl, most preferably hydrogen. Furthermore, each $W^1$ and $W^2$ is preferably hydrogen.

A preferred embodiment of the present invention refers to the compound K-252a conjugated to a polymer moiety. An even more preferred embodiment refers to polymer conjugates of K-252a and derivatives thereof, wherein the chemical group linking the polymer unity to the K-252a compound or to the K-252a derivative compound is characterised by a 5-member oxazolidindionic cyclic structure. Therefore, in a very preferred embodiment of the present invention, the polymer conjugate of formula (I) is represented by a compound wherein $R_1$, $R_2$, $R_3$, $W_1$, and $W_2$ are hydrogen and X is the polymer moiety. According to this very preferred embodiment of the invention the polymer moiety is a polyethylene glycol (PEG) or a methoxy-polyethylene glycol (m-PEG) moiety. Even more preferred the polyethylene glycol or methoxy-polyethylene glycol of the preferred embodiment of the invention is a long-chain PEG or mPEG polymer with an average molecular weight of about 2000 Da or about 5000 Da. Likewise preferred is a short-chain polyethylene glycol or methoxy-polyethylene glycol with an average molecular weight of about 550 Da or about 1100 Da.

The process of the present invention comprises optionally the step of protecting with a protecting group one, more or all the substituents $R_1$, $R_2$, $R_3$, $W_1$ and $W_2$ of the indolocarbazole compound of the K-252a or derivative compound. In this context the term "protecting groups" refers to any derivative of the substituents $R_1$, $R_2$, $R_3$, $W_1$ and $W_2$ known in the art, which can be used, if necessary, to mask $R_1$, $R_2$, $R_3$, $W_1$ and $W_2$ during the synthesis procedure and which can later be removed under conditions resulting in the $R_1$, $R_2$, $R_3$, $W_1$ and $W_2$ substituents being recovered without undesired effects on the remaining of the molecule. In particular—if necessary—a protecting group is introduced on one, more or all of the substituents $R_1$, $R_2$, $R_3$, $W_1$ and $W_2$ during the conjugation process of the invention in order to obtain chemoselectivity of the polymer conjugation on the C3 position of the indolocarbazole structure of the K-252a or derivative compound. After the conjugation reaction, the one or more protecting groups may be reversibly removed in order to give back the original functional group of the involved substituents $R_1$, $R_2$, $R_3$, $W_1$ and $W_2$ obtaining the indolocarbazole conjugated compound of formula (I).

According to the present invention, any suitable protecting group known in the art may be used for this purpose. The choice of the suitable protecting group as well as any suitable means and conditions for protecting and deprotecting the substituents $R_1$, $R_2$, $R_3$, $W_1$ and $W_2$ may be achieved by the skilled person by his general knowledge in the art of organic synthesis. The means and conditions of protecting and deprotecting employed depend on the nature of the involved functional groups $R_1$, $R_2$, $R_3$, $W_1$ and $W_2$. Protecting groups for hydroxy-, amino-, and/or carboxy residues are preferably selected from acetonide, ethylidene methoxymethyl, 2-methoxyethoxymethyl, benzyloxymethyl, tetrahydropyranyl, methyl, ethyl, isopropyl, t-butyl, benzyl, triphenylmethyl, t-butyldimethylsilyl, triphenylsilyl, methoxycarbonyl, t-butyloxycarbonyl, benzyloxycarbonyl, fluorenylmethoxycarbonyl, acetyl, benzoyl, toluenesulfonyl, dimethoxybenzyl, nitrophenyloxycarbonyl, nitrobenzyloxycarbonyl, allyl, fluorenylmethyl, tetrahydrofuranyl, phenacyl, acetol, phenyl, trimethylsilyl, pyrrolidyl, indolyl, hydrazino and other protecting groups known in the art such as those that can be found in Greene T. W., et al., Protective Groups in Organic Synthesis, 4th ed., John Wiley and Son, New York, N.Y. (2007). The reagents and conditions of protecting and deprotecting reactions are in particular selected for their suitability at selectively attaching and removing the protecting group without adversely affecting the rest of the compound. The suitable conditions and reagents are commonly known in the practice of the skilled person.

According to the present invention, the compounds of formula (I) may also be prepared as pharmaceutically acceptable salts including salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, glycolic, gluconic, succinic, aryl sulfonic, (e.g., p-toluene sulfonic acids, benzenesulfonic), phosphoric, malonic, and the like. Suitable acids for formation of pharmaceutically acceptable salts are known to a person skilled in the art. Furthermore, pharmaceutically acceptable salts of compounds of formula (I) may be formed with a pharmaceutically acceptable cation. Pharmaceutically acceptable cations are known to a person skilled in the art and include alkali cations (Li+, Na+, K+), earth alkali cations (Mg2+, Ca2+, Ba2+), ammonium and organic cations, such as quaternary ammonium cations.

A further aspect of the present invention are novel polymer conjugates of K-252a and derivatives thereof, wherein the chemical group linking the polymer unity to the K-252a compound or to the K-252a derivative compound is characterised by a 5-member oxazolidindionic cyclic structure. These novel polymer conjugates are produced by the novel synthetic process disclosed herein.

In particular a further aspect of the present invention is therefore a polymer conjugate of an indolocarbazole compound of formula (I)

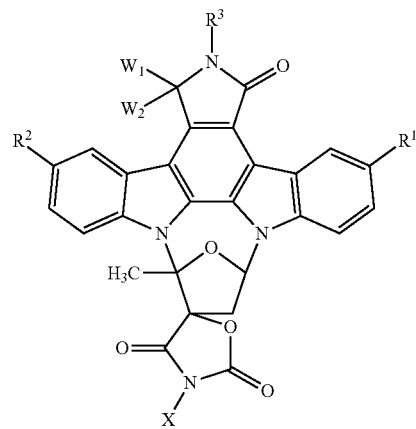

formula (I)

wherein $R_1$, $R_2$, $R_3$, $W_1$ and $W_2$ as well as the polymer moiety X are as defined in detail above or a pharmaceutically acceptable salt thereof.

In a most preferred embodiment the invention relates the a novel polymer conjugate compound of formula (I) wherein $R_1$, $R_2$, $R_3$, $W_1$ and $W_2$ are hydrogen and the polymer moiety X is a polyethylene glycol (PEG) or a terminally alkoxy-substituted PEG, e.g. preferably a methoxy-polyethylene glycol (m-PEG). This compound corresponds to the polymer conjugated compound of K-252a according to the present invention. Preferably the polymer moiety is a long-chain polyethylene glycol, even more preferably a terminally alkoxy-substituted PEG such as methoxy-polyethylene glycol (m-PEG) with an average molecular weight of about 2000 Da or about 5000 Da. Likewise preferably the polymer moiety is a short-chain polyethylene glycol, even more preferably a terminally alkoxy-substituted PEG such as a methoxy-polyethylene glycol (m-PEG) with an average molecular weight of about 550 Da or about 1100 Da.

It was surprisingly found by the inventors of the present application that compared to the members of indolocarbazole compounds and in particular compared to K-252a itself or its derivatives lacking a polymer, the corresponding polymer conjugated compounds of formula (I) exhibit an improved pharmacokinetic and toxicologic performance due to their increased solubility, leading to an improved bioavailability of the therapeutic and biologically active compound. In another aspect of the present invention, it was surprisingly found that the polymer conjugated indolocarbazole compounds of formula (I) show a limited systemic absorption upon topical administration due to their increased molecular size and amphipathicity, thus enhancing the topical therapeutic and biological effectiveness as well as reducing the systemic toxicity and/or side-effects due to topical application.

It has further been surprisingly found by the inventors of the present application that the indolocarbazole-polymer conjugates of formula (I) exhibit a significant increase in selectivity in the inhibitory activity against TrkA tyrosine kinase in comparison with the non-selective kinase inhibitory activity of the indolocarbazole compounds itself and in particular of K-252a and its derivatives lacking a polymer. Thus, the conjugation of an indolocarbazole compound and in particular of K-252a to a polymer molecule according to the invention leads to the provision of an active agent selective with regard to its therapeutic target with the consequent decrease of undesired side effects. Hence, a further aspect of the present invention is the use of compounds of formula (I) as active agents in a medicament. In a preferred aspect of the invention, the compounds of formula (I) are used as active agents in a medicament for systemic administration and treatment. In a likewise preferred aspect, the invention relates to the use of compounds of formula (I) as active agents in a topical medicament.

In particular the conjugated polymer compounds of the present invention are used as active agents in a medicament useful for the prevention, alleviation and treatment of HMGB1-associated pathologies. An HMGB1-associated pathology is a condition in a patient wherein an increased concentration of the nuclear protein HMGB1 and/or of HMGB1 homologous proteins in the acetylated or non-acetylated form is present in the biological fluids and tissues, compared to the concentration in normal subjects where these HMGB1 nuclear proteins are practically undetectable. The extracellular HMGB1s, act as potent chemotactic pro-inflammatory chemokines. The HMGB1-associated pathologies are hence pathologies with a strong inflammatory basis, pathologies which result from the stimulation of cytokine such as TNF-alpha, IL-1, IL-6 etc., or pathologies which result from toxic events such as intoxication, infection, burn, etc. In particular, high concentrations of the HMGB1 protein and homologous proteins have been found and determined in plasma of patients with sepsis, in plasma and synovial fluid of rheumatoid arthritis patients, in brains of Alzheimer's disease patients, in plasma and tissues of melanoma patients, in plasma of systemic lupus erythematosus patients, in atherosclerotic plaques of atherosclerotic patients, etc. The determination and evidence of HMGB1 protein and/or homologous proteins in biological fluids and tissues may be detected by common diagnostic tools known by the skilled person in the art, including, for example, detection by ELISA assays etc.

Therefore, a variety of diseases are characterized by the relevant presence of extracellular HMGB1, which in particular include but are not limited to inflammatory diseases, stenosis, restenosis, atherosclerosis, rheumatoid arthritis, autoimmune diseases, tumors, infective diseases, sepsis, acute inflammatory lung injury, lupus erythematosus, neurodegenerative diseases, diseases of the central and peripheral nervous system and multiple sclerosis. In an especially preferred embodiment, the conjugated polymer compounds of formula (I) are used for the prevention, alleviation and treatment of cardiovascular diseases, particularly atherosclerosis and/or restenosis occurring during or after angioplasty. More preferably, the medicament is used for blocking, retarding and/or impairing connective tissue regeneration in restenosis during or after angioplasty.

In a particularly preferred aspect of the invention, the conjugated polymer compounds of formula (I) are efficient for the use as active agent in a medicament for the prevention, alleviation and treatment of neurological disorders, neuropathies and neurodegenerative disorders of the central and peripheral nervous system.

It was further shown by the inventors that the new polymer conjugate compounds are able to reduce and/or inhibit the plasma cytokine secretion by systemic treatment. Therefore, the polymer conjugate compounds are used as active agents in a medicament for systemic administration useful for the prevention, alleviation and/or treatment of pathologies in which an increase of plasma cytokine secretion is involved. These pathologies are preferably pathologies, in which a secretion of TNF-α, IFN-γ, MCP-1, MIP-1 and/or RANTES are mainly involved.

In particular, in the context of the present invention, pathologies which are associated with an increased plasma cytokine secretion include but are not limited to inflammatory diseases, autoimmune diseases, systemic inflammatory response syndrome, reperfusion injury after organ transplantation, cardiovascular affections, obstetric and gynecologic diseases, infectious diseases, allergic and atopic diseases, solid and liquid tumor pathologies, transplant rejection diseases, congenital diseases, dermatological diseases, neurological diseases, cachexia, renal diseases, iatrogenic intoxication conditions, metabolic and idiopathic diseases, and ophthalmological diseases.

In a most preferred embodiment, the compounds of the invention are used as active agents in a medicament for systemic treatment useful for the prevention, alleviation and/or treatment of Behçet's disease, Sjögren's syndrome, vasculitis, uveitis, retinopathies.

In yet another particular aspect of the invention, it is preferred that the conjugated polymer compounds of the present invention are used as active agents in a topical medicament useful for the prevention, alleviation and/or treatment of dermal pathologies. It has been shown by the inventors of the present invention that the conjugated polymer compounds described herein are very advantageously used as topical medicament since they do not show adverse or toxic effects (e.g. irritation) when dermally administered or any phototoxic effect (e.g. photomutagenicity, phototoxicity or photosensitisation) (as shown in the studies described in the following examples).

The dermal pathologies preferred in the context of the present invention are pathologies characterized by hyperproliferation of the keratinocytes, such as psoriasis, atopic dermatitis, chronic eczema, acne, pitiriasis rubra pilaris, keloids, hypertrophic scars and skin tumors, such as keratoacanthoma, squamous cell carcinoma, basal cell carcinoma. In a more preferred embodiment, the compounds of the present invention are used as active agents in a topical medicament useful for the prevention, alleviation and treatment of psoriasis.

Due to the increased selectivity of the compounds of the invention in the inhibition of TrkA, a further aspect of the invention is the use of said conjugated compounds in the prevention, alleviation and treatment of pathologies in which TrkA plays a crucial role in the pathophysiological mechanism, which leads to the development of the pathologies. In this context, in a very preferred embodiment of the invention, the conjugated K-252a polymer compounds of formulae (I), (II), and/or (III) are used as active agent in a medicament for the prevention, alleviation and treatment of NGF-related pain and hyperalgesia.

Hence, a further aspect of the present invention is the use of a compound of formula (I) as defined above optionally together with pharmaceutically acceptable carriers, adjuvants, diluents or/and additives for the manufacture of a medicament for the prevention, alleviation or/and treatment of pathologies as defined above.

The compounds of formula (I) or pharmaceutically acceptable salts thereof can be administered as they are, or in the form of various pharmaceutical compositions according to the pharmacological activity and the purpose of administration. Yet another aspect of the present invention is a pharmaceutical composition comprising an effective amount of at least one compound of formula (I) optionally together with pharmaceutically acceptable carriers, adjuvants, diluents or/and additives. Pharmaceutical carriers, adjuvants, diluents or/and additives are known to a person skilled in the art and may therefore be applied in the formulation of the pharmaceutical composition comprising a compound of the present invention.

The compounds of this invention can be employed as the sole active agent in a pharmaceutical composition. Alternatively, the compounds of formula (I) may be used in combination with one or several further active agents, e.g. other active pharmaceutical agents in the treatment of the above defined pathologies.

In particular, the polymer conjugate compounds of the invention may be used in combination with at least one steroidal anti-inflammatory drug and/or one further agent capable of inhibiting an early mediator of the inflammatory cytokine cascade, e.g. an antagonist or inhibitor of a cytokine selected from the group consisting of TNF, IL-1α, IL-1β, IL-$R_a$, IL-8, MIP-1α, MIF-1β, MIP-2, MIF and IL-6. Particularly useful anti-inflammatory drugs are selected from alclometasone dipropionate, amcinonide, beclomethasone dipropionate, betamethasone, betamethasone benzoate, betamethasone dipropionate, betamethasone sodium phosphate, betamethasone sodium phosphate and acetate, betamethasone valerate, clobetasol butyrate, clobetasol propinate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, diflucortolone valerate, fludrocortisone acetate, fludroxycortide, flumetasone pivalate, flunisolide, fluocinolone acetonide, fluocinonide, fluocortolone, fluorometholone, flurandrenolide, fluticasone propionate, halcinonide, halobetasol propionate, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetate, triamcinolone acetonide, triamcinolone diacetate, triamcinolone hexacetonide. Useful antagonists or inhibitors of a cytokine are selected from infliximab, etanercept or adalimumab.

Further agents which can be used in combination with the polymer compounds of the invention are e.g. antagonists and/or inhibitors of RAGE, antagonists and/or inhibitors of HMGB1, antagonists and/or inhibitors of the interaction of a Toll-like receptor (TCR) with HMGB1, the functional N-terminal lectin-like domain (D1) of thrombomodulin and/or a synthetic double-stranded nucleic acid or nucleic acid analogue molecule with a bent shape structure as described in the international patent application WO 2006/002971 which is herein incorporated by reference.

The pharmaceutical composition of the present invention may be administered in a convenient manner known by a person skilled in the art, e.g. by a physician. In particular, the pharmaceutical composition of the invention may be administered by injection or infusion, in particular by intravenous, intramuscular, transmucosal, subcutaneous or intraperitoneal injection or infusion and/or by oral, topical, dermal, nasal, inhalation, aerosol and/or rectal application, etc. The administration may be local or systemic. Preferably, the administration of the compound and the pharmaceutical composition of the invention may be performed by parenteral administration, particularly in the form of liquid solutions or suspensions; or oral administration, particularly in the form of tablets or capsules, or intranasally, particularly in the form of powders, nasal drops, or aerosols; or dermally, via, for example, ointments, creams, oils, liposomes or trans-dermal patches.

According to one aspect of the invention, the pharmaceutical composition is administered systemically. In particular, the polymer conjugate compounds can be administered by injection or infusion, in particular by intravenous, intramuscular, transmucosal, subcutaneous or intraperitoneal injection or infusion and/or by oral administration.

In a still most preferred embodiment, the pharmaceutical composition of the present invention are administered by topical application, in particular by dermal application. In case of a dermal application the administration of the compounds of the present invention may be performed in the form of liposomes.

In a further most preferred embodiment of the invention, the pharmaceutical composition are administered reversibly immobilized on the surface of a medical device, in particular by binding, coating and/or embedding the compound and composition of the invention on a medical device, such as but not limited to, stents, catheters, surgical instruments, cannulae, cardiac valves, or vascular prostheses. After contacting the medical device with body fluid or body tissue, the reversibly immobilised compounds are liberated. Consequently, the coated medical devices act as drug delivery devices eluting the medicament, whereby the drug delivery kinetics can be controlled, providing an immediate release or a controlled, delayed or sustained drug delivery, for example. Coating technologies of medical devices are well known to the person skilled in the art.

The pharmaceutical composition of the present invention may be used for diagnostic or for therapeutic applications. For diagnostic applications, the compound of formula (I) may be present in a labelled form, e.g. in a form containing an isotope, e.g. a radioactive isotope or an isotope which may be detected by nuclear magnetic resonance. A preferred therapeutic application is, in the case of a topical application, the prevention, alleviation and treatment of psoriasis and dermatitis, while in the case of a systemic application, the prevention, alleviation and treatment of connective tissue regeneration in restenosis.

The concentrations of the compounds of this invention in the pharmaceutical composition can vary. The concentration will depend upon factors such as the total dosage of the drug to be administered, the chemical characteristics (e.g., hydrophobicity) of the compounds employed, the route of administration, the age, body weight and symptoms of a patient. The compounds of this invention typically are provided in an aqueous physiological buffer solution containing about 0.1 to 10% w/v compound for parenteral administration. Typical dose ranges are from about 1 µg to about 1 g/kg of body weight per day; a preferred dose range is from about 0.01 mg/kg to 100 mg/kg of body weight per day, and preferably about 0.1 to 20 mg/kg once to four times per day. A preferred dosage of the drug to be administered is likely to depend on variables such as the type and extent of the progression of the disease or disorder, the overall health status of the particular patient, the relative biological efficacy of the selected compound and the formulation of the compound excipient, and its route of administration.

The improved synthesis method according to the present invention should be explained further by the following figure and example, which should, however, not limit the subject-matter of the present invention.

FIG. 1 shows a preferred embodiment of the process according to the present invention. The indolocarbazole compound K-252a is reacted with a α-methoxy-ω-1H-imidazole-carboxamide polyethylene glycol (mPEG-NH-CO-Im) in order to give a methoxy polyethylene glycol conjugate of K-252a according to the invention. In this preferred compound of the invention the methoxy-polyethylene glycol is covalently attached to the active K-252a compound via the 5-member oxazolidindionic cyclic structure.

EXAMPLES

Example 1

Synthesis of α-methoxy-ω-1H-imidazole-carboxamide polyethylene glycol (mPEG-NH-CO-Im)

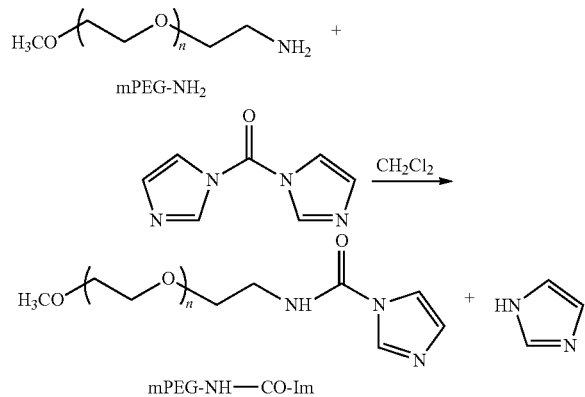

In a 500 ml volume round bottom flask, 35.0 g of mPEG-NH$_2$ (MW 1892) (assay 96%, 17.76 mmol) were dissolved in 85 ml of dichloromethane in nitrogen atmosphere. The solvent was removed under reduced pressure and the compound was dried by mechanical pump for two hours. The substrate was then dissolved in 150 ml of dichloromethane in nitrogen atmosphere and the solution was transferred in a 2 l volume three necks round bottom flask.

4.80 g of 1,1-carbonyldiimidazole (assay 90%, 26.64 mmol) were added to the solution at room temperature. The mixture was stirred at room temperature in nitrogen atmosphere and checked by TL chromatography (eluent CH$_2$Cl$_2$/MeOH 90:10). The TLC was treated with ninhydrin solution in order to spotlight the presence of the primary amine group (violet colour).

The reaction was complete within two hours. The mixture was cooled at 0° C. and the solid product was precipitated by slow addition of diethyl ether (700 ml in 60 min) under vigorous stirring. The mixture was stirred for 30 minutes at 0° C. and further 300 ml of diethyl ether were added. The product was filtered over glass sintered disc filter funnel, washed with 100 ml of diethyl ether and dried under vacuum. 34.0 g of dry white solid were obtained (yield 94%).

The product was characterized by $^1$H-NMR and ESI-MS.

$^1$H-NMR (DMSO-d$_6$) δ (ppm): 8.24 (m, 1H, CH), 7.69 (m, 1H, CH), 7.27 (s, 1H, NH), 7.02 (s, 1H, CH), 3.55 (m, CH$_2$ PEG), 3.40 (m, 2H, CH$_2$NH), 3.22 (s, 3H, OCH$_3$).

ESI-MS (Cluster +2) . . . 944.4, 966.4, 988.5, 1010.5, 1032.5 . . . (mass increase +47 with respect to cluster +2 of mPEG-NH$_2$ . . . 897.4, 919.4, 941.5, 963.5, 985.5).

Example 2

Figure 1:
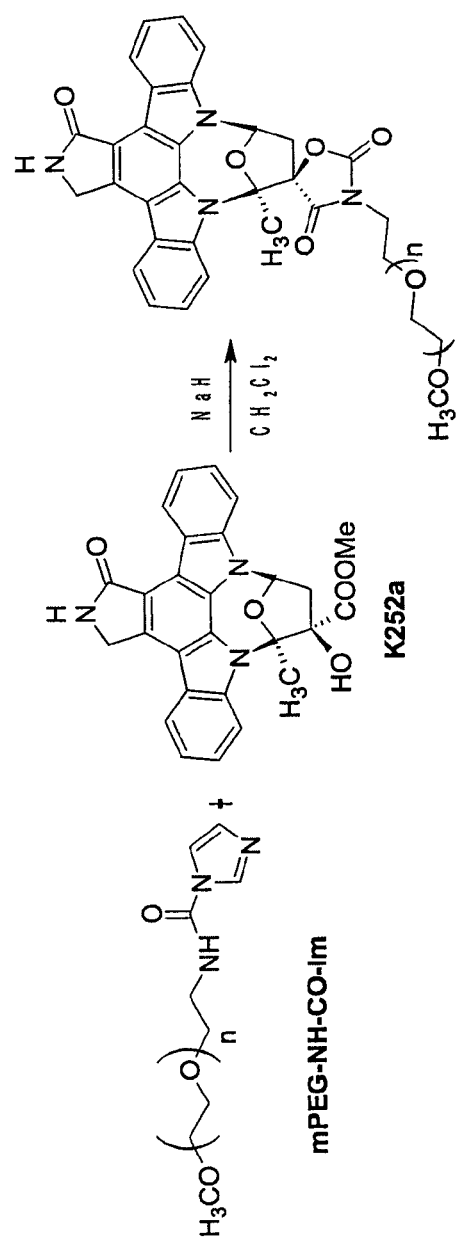
Figure 2:
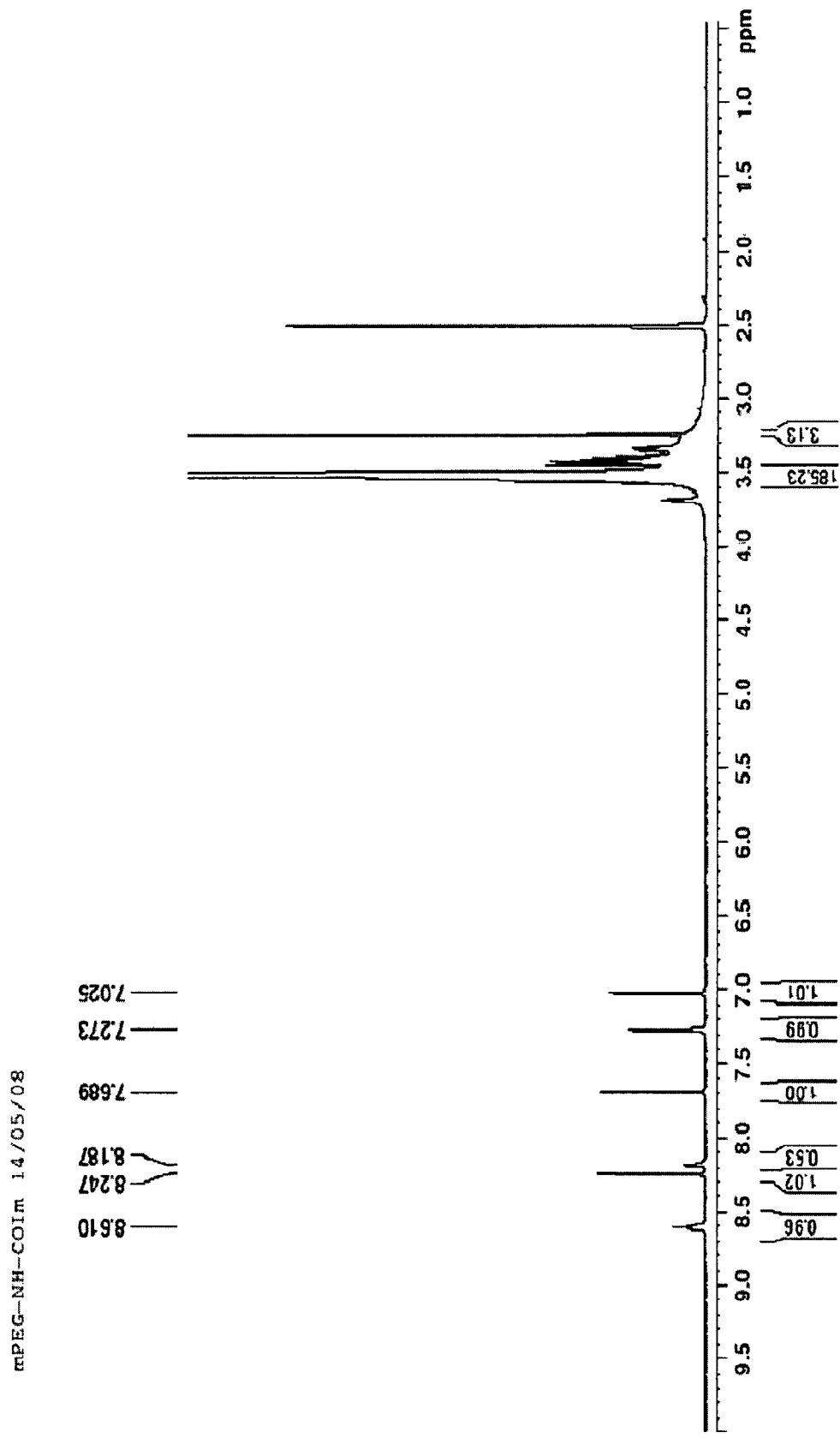
FIG. 2 shows the $^1$H-NMR spectrum of the activated polymer mPEG-NH-CO-Im in DMSO-d6 solvent at a magnetic field of 400 MHz.
Figure 3:
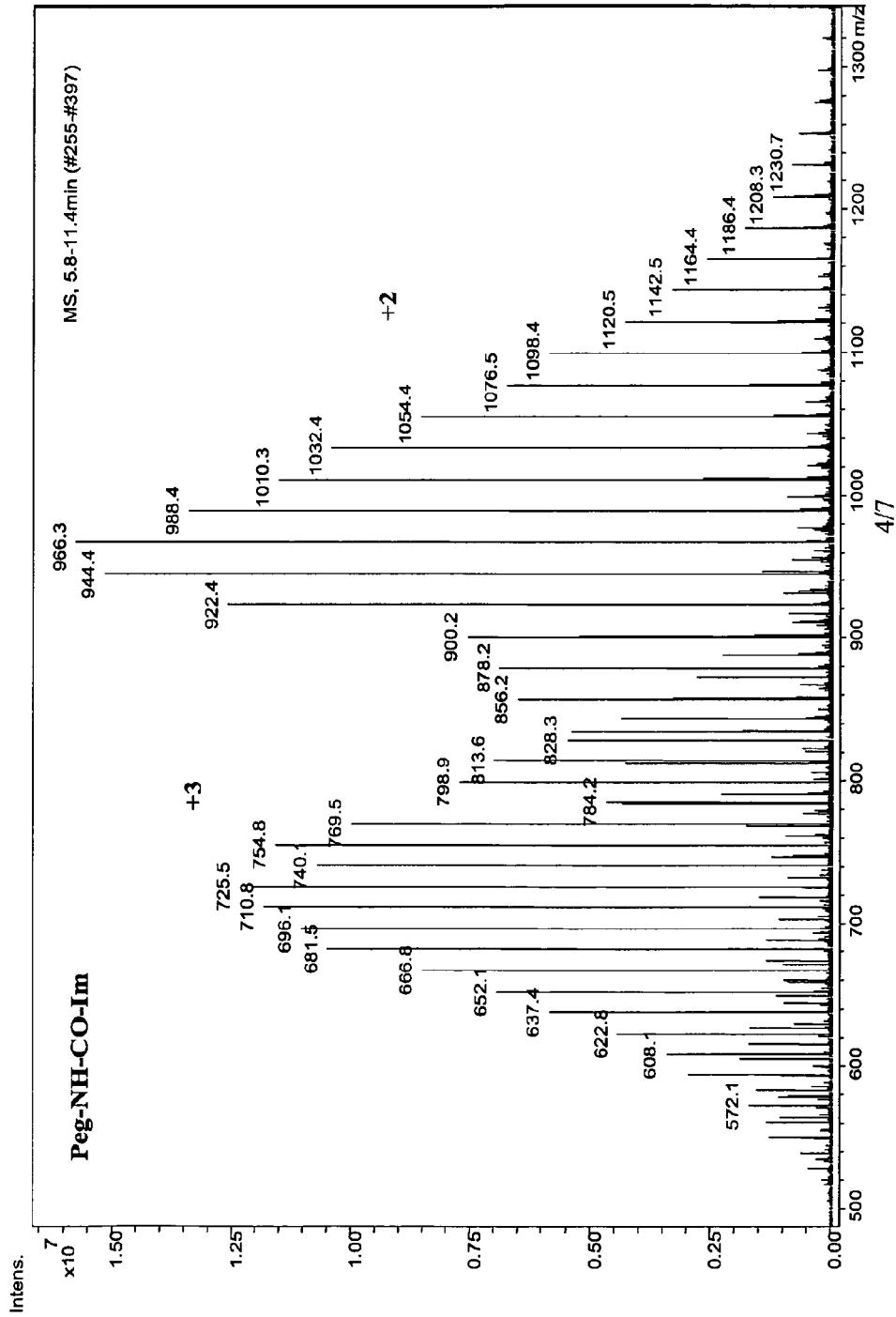
FIG. 3 shows the ESI-MS spectrum of mPEG-NH-CO-Im in the range 500-1400 m/z using direct infusion ion trap electrospray ionization.
Figure 4:
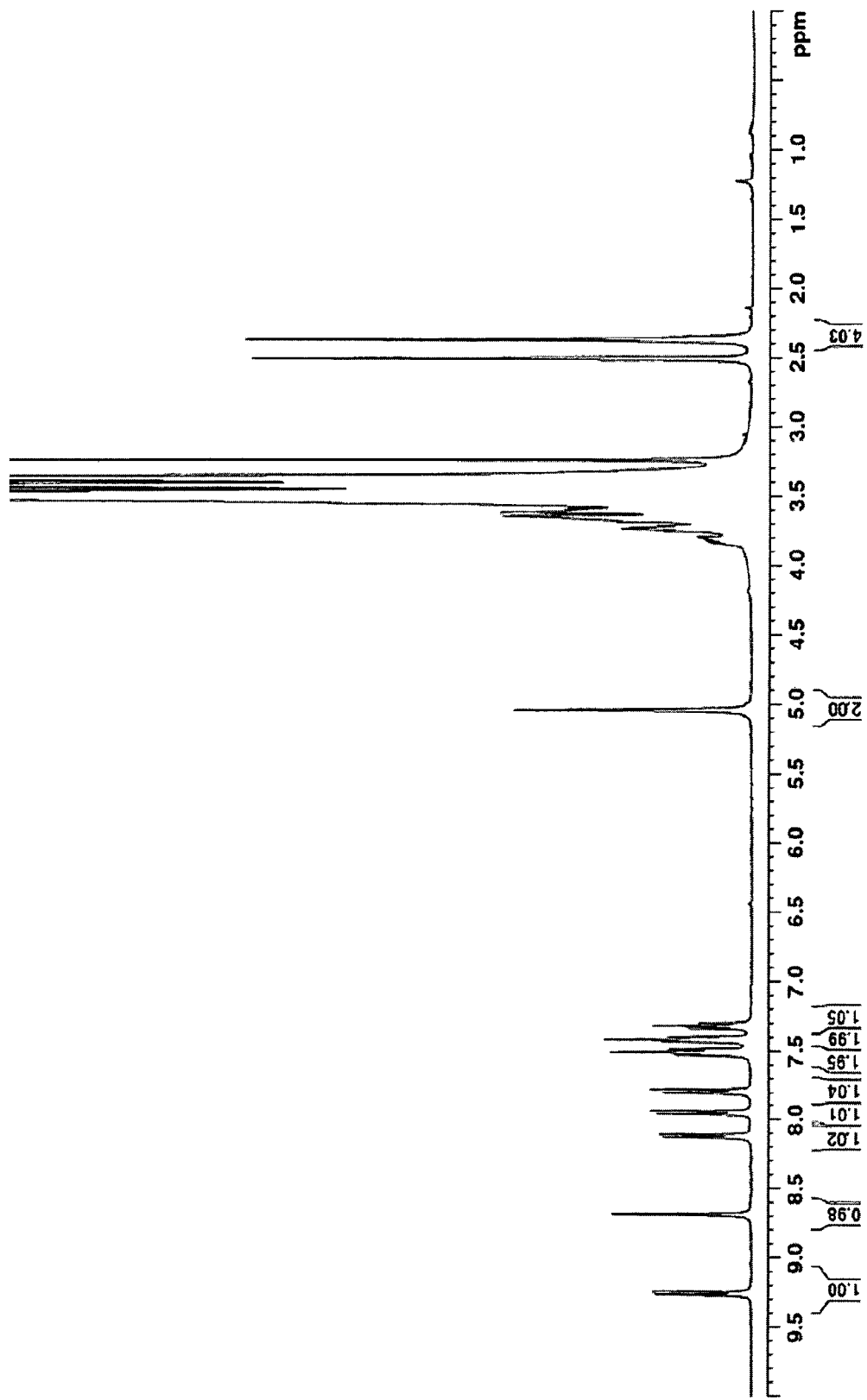
FIG. 4 shows the $^1$H-NMR spectrum of the K-252a polymer conjugate of FIG. 1 in DMSO-d6 solvent at 400 MHz.
Figure 5:
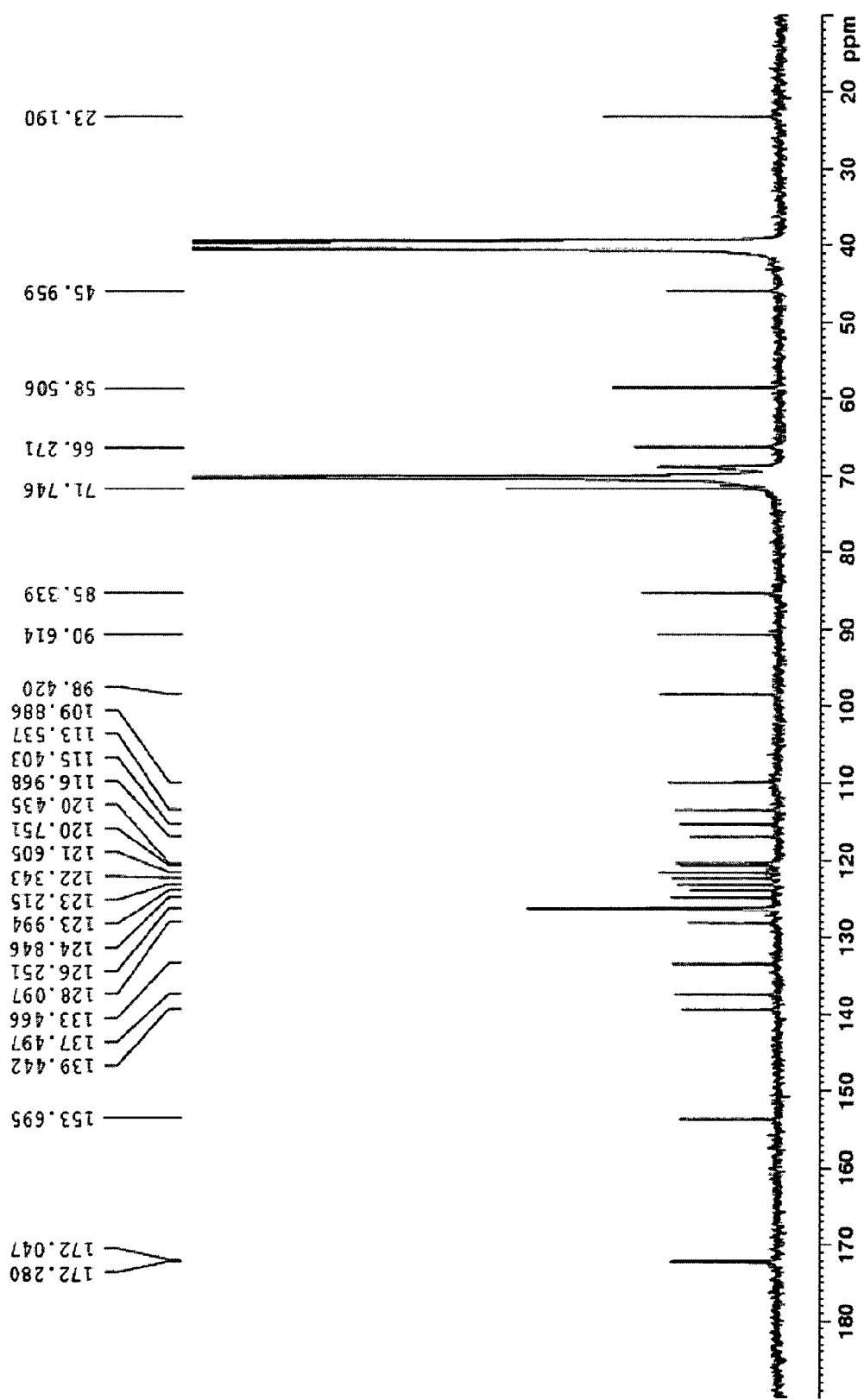
FIG. 5 shows the $^{13}$C-NMR spectrum of the K-252a polymer conjugate of FIG. 1 in DMSO-d6 solvent at 400 MHz.
Figure 6:
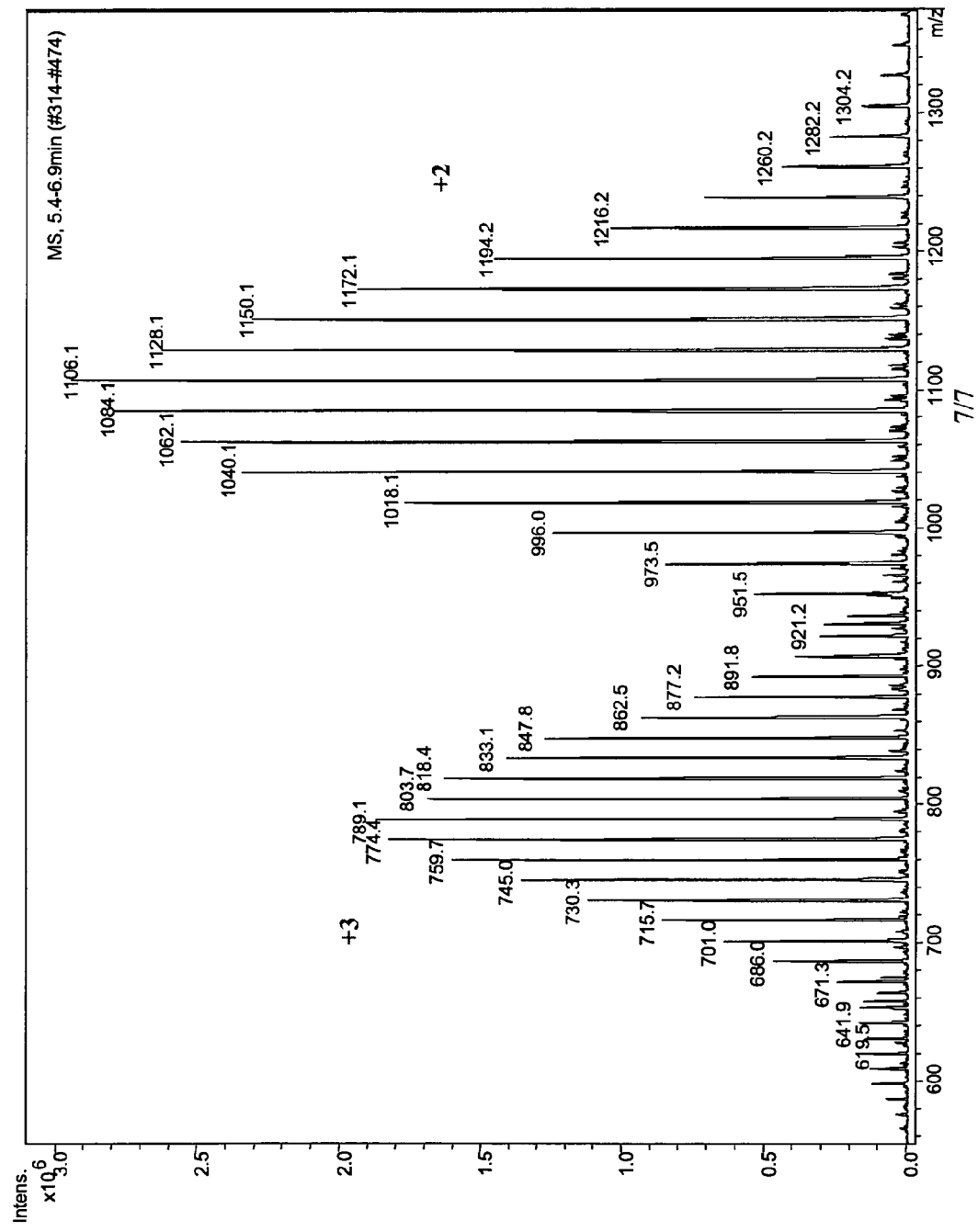
FIG. 6 shows the ESI-MS spectrum of the K-252a polymer conjugate of FIG. 1 in the range 500-1400 m/z using direct infusion ion trap electrospray ionization.

Polymer Conjugation Reaction of the K-252a for the Manufacture of an Oxazolidindionic Conjugate The scheme of the process is reported in FIG. 1.

In a 500 ml volume round bottom flask 33.0 g of mPEG-NH-CO-Im (16.00 mmol) were dissolved in 85 ml of dichloromethane in nitrogen atmosphere. The solvent was removed under reduced pressure and the compound was dried by mechanical pump for two hours.

In a 2 l volume reactor equipped with thermo cryostat unit, mechanical stirrer and thermometer, 6.21 g of K-252a (assay 98%, 13.29 mmol) were dissolved in 1.85 L of dichloromethane under nitrogen atmosphere and the solution was cooled to 0° C. 0.53 g of sodium hydride (assay 60%, 13.29 mmol) were added in nitrogen atmosphere and the mixture was stirred for 10 minutes. The dried mPEG-NH-CO-Im was dissolved in 90 ml of dichloromethane and the solution was added to the mixture of K-252a and NaH in dichloromethane at 0° C. in nitrogen atmosphere. The mixture was stirred for 30 minutes at 0° C., then was heated to 25° C. and kept under stirring at this temperature for 10 minutes.

The reaction mixture was analyzed by HPLC in order to evaluate the conversion of K-252a and the ratio of the compounds in the mixture. After 10 minutes at 25° C. 3.60 g of 1,1-carbonyldiimidazole (assay 90%, 19.93 mmol) were added to the reaction mixture and the solution was stirred at 25° C. for 30 minutes. The reaction mixture was analyzed by HPLC in order to verify the conversion of the amide by-product (mPEG conjugate by the carboxylic moiety in position 9 of K-252a) into the desired oxazolidindionic conjugate. The reaction mixture was neutralized with formic acid (assay 98%) to final pH 6 (about 2 ml, 53 mmol).

The solvent was removed under reduced pressure at 25° C. and 44.0 g of light yellow crude product were obtained.

The HPLC purity of the conjugate in the crude product was above 90%. The content of the desired product in the crude mixture is about 65-70% w/w.

Example 3

Purification of the Oxazolidindionic Conjugate of K-252a by Reversed Phase Flash Chromatography The crude mixture obtained in the conjugation step of Example 2 was purified by reverse phase flash chromatography. A Biotage Horizon system equipped with a Flash 65iM KP-C18 cartridge was used. The production batch was divided into 15 aliquots of 3.0 g each. The aliquots were separately treated.

C18 column was conditioned firstly with 200 ml of solvent by applying the following gradient: from 100% acetonitrile to acetonitrile/water 40:60 and then with 200 ml of acetonitrile/5 mM ammonium formate pH 3.5 40:60, in isocratic conditions.

3.0 g of crude product were dissolved in 3.0 ml of N,N-dimethylformamide and the solution was loaded on the column. The purification was carried out by isocratic elution with acetonitrile/5 mM ammonium formate pH 3.5 40:60. Collected individual fractions were analyzed by HPLC and pure fractions combined. The solvent was removed under reduced pressure at 25° C. and about 2 g of pure wet product were obtained.

Each aliquot was purified following the former procedure and finally each pure wet product fractions were dissolved in 10 ml of dichloromethane and then combined. The solution was dried over sodium sulphate. The solid was filtered off and the solvent was removed under reduced pressure at 25° C.

The obtained solid product was analyzed by NMR spectroscopy and about 1 moleq of ammonium formate was detected. In order to remove this salt the product was dissolved in 50 ml of dichloromethane and eluted over a silica gel pad wetted with dichloromethane. The product was recovered by elution with 700 ml of the solvent mixture dichloromethane/methanol 9:1. The eluate was collected and the solvent was removed under reduced pressure at 25° C. The product was dissolved again in 80 ml of dichloromethane and precipitated at 0° C. under vigorous stirring by addition of 500 ml of diethyl ether in order to obtain a solid product. The product was filtered over glass sintered disc filter funnel, washed with 100 ml of diethyl ether and dried under vacuum for 16 h.

16.0 g of light yellow powder were obtained with an overall yield (conjugation+purification) of 51%.

The product was characterized by NMR, ESI-MS and HPLC. The assay was determined by NMR using an internal standard and corresponded to 101% w/w.

$^1$H-NMR (DMSO-d$_6$) δ (ppm): 9.25 (d, 1H, CH), 8.70 (s, 1H, NH), 8.11 (d, 1H, CH), 7.95 (d, 1H, CH), 7.70 (d, 1H, CH), 7.51 (m, 2H, CH), 7.42 (m, 2H, CH), 7.31 (m, 1H, CH), 5.05 (s, 1H, NHCH$_2$), 3.90-3.40 (m, CH$_2$ PEG), 3.25 (s, 3H, OCH$_3$), 2.35 (m, 4H, CH$_3$+1h CH$_2$).

$^{13}$C-NMR (DMSO-d$_6$) δ (ppm): 172.3, 172.0, 153.7, 139.4, 137.5, 133.5, 128.1, 126.2, 124.9, 124.0, 123.2, 122.3, 121.6, 120.8, 120.4, 117.0, 115.4, 113.5, 109.9, 98.4, 90.6, 85.3, 71.8, 70.0, 68.9, 66.3, 58.5, 45.9, 40.0, 23.16.

ESI-MS (Cluster +2) . . . 1128.2, 1150.3, 1172.3, 1194.3, 1216.3 . . . (mass increase +230.8 with respect to cluster +2 of mPEG-NH$_2$ . . . 897.4, 919.4, 941.5, 963.5, 985.5).

Exact mass: mass exact discrepancy between recorded spectrum and theoretical spectrum corresponds to 2 ppm. Hence, the resultant polymer compound has a purity of at least about 98%.

Example 4

Purification of the Oxazolidindionic Conjugate of K-252a by Normal Phase Flash Chromatography A synthetic process as described in the above Examples 1 and 2 was carried out and in this synthetic run 21.7 g of crude product were obtained.

The crude mixture obtained from said conjugation step was purified by normal-phase flash chromatography using a Biotage Horizon System equipped with a SNAP cartridge packed with 340 g of KP-SIL (Silica) (size 71×168 mm). The crude product was divided into two aliquotes that were purified separately one time each (each aliquote respectively 10.86 g and 10.8 g of the crude).

The SNAP cartridge was equilibrated with 940 ml of dichloromethane/methanol 96:4 v/v. Flow rate was 65 ml/min.

Sample loading was performed using a pre-packed SNAP samplet cartridge (34 g) by dissolving crude material in 10 ml of dichloromethane, applying the solution to the samplet cartridge and inserting the samplet into the SNAP cartridge.

The SNAP cartridge was eluted, at 65 ml/min flow rate, with:
705 ml of dichloromethane/methanol 96:4 v/v;
1881 ml of dichloromethane/methanol 93:7 v/v;
942 ml of dichloromethane/methanol 85:15 v/v.

The first 999 ml of eluted solvent were sent to the waste, then the eluted solvent was collected in 111 ml volume fractions.

Collected individual fractions were analyzed by HPLC and fractions containing the conjugated product compound with HPLC purity >98% (pure fractions) were combined.

The residual aliquot of 10.8 g of the crude mixture material from conjugation step was analogously purified.

Selected fractions from the purifications of the two aliquots of crude mixture were combined, the solvent was removed under reduced pressure at 25° C. to dryness, affording 8.11 g of conjugate product, which was dissolved again in 29 ml of dichloromethane, cooled to 2° C. and precipitated under vigorous stirring by addition of 150 ml of diethyl ether in 15 minutes. The mixture was stirred at 2° C. for 15 minutes, then 225 ml of diethyl ether were added. The precipitated solid was isolated by filtration over sintered glass filter (G4), and dried under vacuum at 25° C. for 16 h to afford 6.95 g of test item as a white to slightly yellow solid. Purity, determined by HPLC analysis, was 99%.

Example 5

Synthetic Process for the Oxazolidindionic Conjugate of K-252a

1) Synthesis of MeO-PEG-NH-CO-Im

MeO-PEG-NH$_2$ (MW1892, 8.06 g) was dissolved in dichloromethane (25 ml) under a nitrogen atmosphere and the solvent was removed by distillation under a reduced pressure at 40° C. The residue (MeO-PEG-NH$_2$) was then dried under vacuum (<40 mbar) at 40° C. for over 2 hours.

The dried MeO-PEG-NH$_2$ (from above) was dissolved in dichloromethane (35 ml) at 25° C. under nitrogen atmosphere and 1,1'-carbonyldiimidazole (1.02 g) was added to the solution and the mixture was stirred at room temperature for over 2 hours. (Ion-Pairing Chromatography (IPC): ≥95% conversion)

The reaction mixture was cooled to 0° C., then 230 ml of diethyl ether were added over 1 hour under vigorous stirring. The mixture was stirred for 30 min at 0° C. and further 69 ml diethyl ether were added over 25 mins. The filter cake was washed twice with diethyl ether (23 ml) and dried under vacuum at max 40° C. to constant weight to achieve 8.25 g of MeO-PEG-NH-CO-Im as a white solid.

2) Polymer Conjugation Reaction

MeO-PEG-NH-CO-Im (72.0 g) was dissolved in dichloromethane (185 ml) under nitrogen atmosphere and the solvent was removed by distillation under reduced pressure at 40° C. The residue was dried under a vacuum (<40 mbar) at 40° C.>2 hours.

K252a (13.11 g) was dissolved in dichloromethane (3920 ml) and the solution was then cooled to 0° C. Sodium hydride (1.17 g of 60%) was added portion wise.

The dried MeO-PEG-NH-CO-Im was dissolved in dichloromethane (140 ml) and the solution was added at <5° C. to the reaction mixture of K252a and the mixture was stirred for >30 min at 0° C. The mixture solution was then heated to 25° C. and kept stirring at this temperature for 10 minutes. (IPC 1: conversion of K252a>96%).

1,1'-carbonyldiimidazole (7.11 g) was added to the reaction mixture and the solution was stirred at 25° C. for >30 minutes (IPC 2: ratio crude product:amide>80:20).

Formic acid (5 ml) was added to adjust to pH 6 of the reaction mixture. The solvent was removed by distillation at 25° C. under reduced pressure and the residue was dried under a vacuum at 25° C. to constant weight.

3: Purification and Isolation of the Polymer Conjugate

The crude mixture (81 g) was dissolved in 325 ml dichloromethane at <35° C. for over 15 minutes and filtered over a Celite bed (3 cm). The Celite was washed with 81 ml dichloromethane. The solvent is removed by distillation under reduced pressure at <35° C. and dried to constant weight under 35° C. to achieve 77.0 g solid material. The solid material was dissolved in 770 ml dichloromethane.

The crude material from Example 5.2 is purified on a Knauer preparative HPLC system using Flash KP-SIL 75 L cartridges (75×300 mm, 800 g silica) from Biotage. Prior to applying the feed solution the cartridges were purged with 1.5 l n-heptane and equilibrated with 3 l of DCM:MeOH=96:4 (v:v). For each run 200 ml of the above described feed solution DCM:MeOH=96:4 (v:v) (Loading 20 g) was injected and the elution was started with a flow of 185 ml/min and the gradient described below.

| Minutes | % MeOH |
|---|---|
| 0.00 | 4 |
| 8.30 | 4 |
| 80.10 | 15 |
| 80.10 | 50 |
| 108.00 | 50 |

Each cartridge was just used for one run. The product was eluting between 25 and 90 min. Fractions were collected analyzed and pooled according to their purity (IPC: >98% a/a).

The solvent is then removed under reduced pressure at 35° C. The solids are dried to constant weight under vacuum at 35° C. to obtain crude material (37.92 g). The material is dissolved in 140 ml dichloromethane and cooled to 2° C. 700 ml diethyl ether is added at 2° C. and stirred for >15 minutes. 1050 ml diethyl ether is added at 2° C.

The suspension is filtered via a suction filter. The filter cake washed with the mother liquor and dried to constant weight to obtain 32.6 g purified drug substance. The purity obtained according to HPLC analysis was 98.99%.

The further examples describe several studies performed with the polymer conjugate indolocarbazole compound of the invention, in particular with the polymer conjugate obtained through the synthetic process of the invention, e.g. as described in Examples 1-5. The tested conjugate compound (also designated "test item") is the oxazolidindionic conjugate of K252a with PEG (1892 MW).

Example 6

In Vitro Evaluation of $IC_{50}$ Against TrkA for the Oxazolidindionic Conjugate of K-252a The purpose of this study was to measure $IC_{50}$ for the conjugate of Example 3 against TrkA kinase. The test compound was dissolved in dimethylsulfoxide (DMSO) and then the solution was further 25-fold diluted with assay buffer to make the final test compound solution. The conjugate was tested at the following concentrations: 30000 nM, 10000 nM, 3000 nM, 1000 nM, 300 nM, 100 nM, 30 nM, 10 nM, 3 nM and 1 nM.

Reference compound (Staurosporine) for assay control was prepared similarly to the method used for the preparation of the test compound.

The assay procedure is represented by an Off-chip Mobility Shift Assay (MSA) and is reported below:
1) The 5 μl of ×4 compound solution, 5 μl of ×4 substrate (CSKtide 1000 nM)/ATP (75 μM)/metal solution (Mg 5 mM), and 10 μl of ×2 kinase solution were prepared with assay buffer [20 mM HEPES (4-(2-hydroxyethyl)-1-piperazineethanesulfonic acid), 0.01% Triton X-100, 2 mM DTT (1,2-dithio-treitol), pH7.5] and mixed and incubated in a well of polypropylene 384 well microplate for 1 or 5 hour(s)* at room temperature. (*; depend on kinase)
2) 60 μl of Termination Buffer (QuickScout Screening Assist MSA; Carna Biosciences) was added to the well
3) The reaction mixture was applied to LabChip3000 system (Caliper Life Science), and the product and substrate peptide peaks were separated and quantitated
4) The kinase reaction was evaluated by the product ratio calculated from peak heights of product (P) and substrate (S) peptides (P/(P+S)).

The readout value of reaction control (complete reaction mixture) was set as a 0% inhibition, and the readout value of background (Enzyme(−)) was set as a 100% inhibition, then the percent inhibition of each test solution was calculated. $IC_{50}$ value was calculated from concentration vs. % inhibition curves by fitting to a four parameter logistic curve. The kinase reaction was evaluated by the product ratio calculated from peak heights of product (P) and substrate (S) peptides (P/(P+S)).

Figure 7:
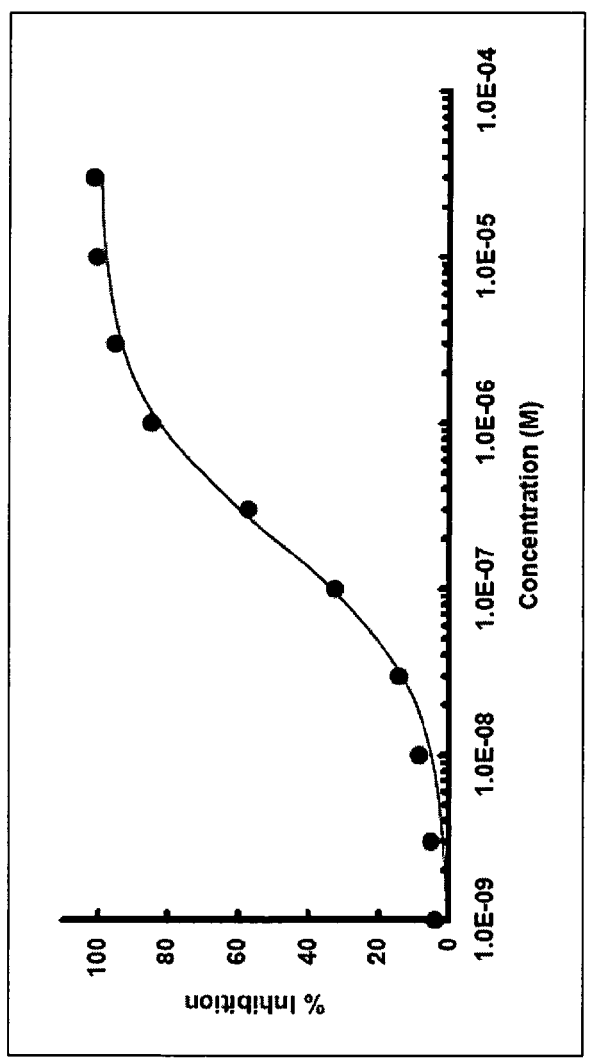
FIG. 7 shows the inhibition curve of the K-252a polymer conjugate of FIG. 1 against TrkA.

IC50 value of the conjugate against TrkA was 202 nM, the corresponding IC50 value of reference compound (Staurosporine) against TrkA was 0.372 nM. These results are summarized in FIG. 7.

Example 7

Acute Dermal Toxicity Study in Rats

The acute toxicity of the conjugate of Example 3 was investigated following administration of a single dermal dose to the rat.

A single dose of 2000 mg/kg was administered to a group of 5 male and 5 female animals for a 24 hour period. The day before scheduled dosing the fur was removed from the dorsal surfaces of the trunk over an estimated area of 10% of the total body surface. Care was taken to avoid any damage or abrasion to the skin. The test item was administered topically at a dose volume of 4 ml/kg body weight, just after its preparation. The required aliquot of the formulated test item was spread evenly over a gauze measuring 2.5×2.5 cm. The gauze patch was then placed onto the animal's skin, with the test item in direct contact with the skin. A strip of synthetic film was placed over the treated site and the whole assembly held in place by encircling the trunk of the animal with a length of elastic adhesive bandage. After a period of 24 hours, the tape dressing will be removed. The treated skin site was then gently washed free of any remaining test item using lukewarm water. Throughout the study, all animals will be checked twice daily. Animals were examined for signs of reaction to treatment on dosing, approximately 30 min, 2 and 4 hours after dosing on day 1, then daily for a total of 14 days. Each animal was weighed on the day of allocation to the study, on the day of dosing (day 1) and on days 8 and 15. After a 14 day period all animals were killed and subjected to a necropsy examination.

No mortality occurred and no clinical signs were observed in male or female animals during the study. Changes in body weight observed in the animals at the end of the study were within the expected range for this species and age of animals. No internal abnormalities were found at necropsy in the animals at termination of the study. No abnormalities were observed in the treated site.

These results indicate that the test compound has no toxic effect on the rat following dermal exposure over a 24 hour period at a level of 2000 mg/kg. The lack of mortality demonstrates the $LD_{50}$ to be greater than 2000 mg/kg.

Example 8

13 Week Dermal Toxicity Study in Rats Followed by a 4 Week Recovery Period

The purpose of this study was to evaluate the toxicity of the test item in rats after daily dermal administration (6 hours exposure) over a period of 13 weeks and to investigate possible recovery from any potential treatment-related effects over a period of 4 consecutive weeks. The toxicokinetic profile was also evaluated.

Three groups, each of 10 male and 10 female Sprague Dawley rats (cf. Table 1: male numbered with even numbers, female numbered with uneven numbers) received the test item by dermal application at dosages of 0.5, 2.5 and 5 mg/kg/day for 13 consecutive weeks (Table 1: group numbers 2-4). A fourth similarly constituted group received the vehicle alone (purified water) and acted as a control (Table 1: group number 1). Five additional animals for each sex were included in the high and control groups (Table 1: group numbers 4 and 1, respectively) for recovery assessment. In addition, 3 satellite groups for toxicokinetics, including 9 males and 9 females (Table 2: group numbers 5-8, respectively), and 1 control group, including 3 males and 3 females (Table 2: group number 5), were treated as the main groups for toxicokinetic evaluations.

The group identification and animal numbers assigned to treatment are summarised below in Table 1 and 2:

Table 1 (Main Groups):

TABLE 1

| | | | Rat numbers | | | |
|---|---|---|---|---|---|---|
| | | | Main phase | | Recovery phase | |
| Group Number | Treatment (mg/kg/day) | Level | M (even) | F (odd) | M (even) | F (odd) |
| 1 | 0 | Control | 2-20 | 1-19 | 22-30 | 21-29 |
| 2 | 0.5 | Low | 32-50 | 31-49 | | |
| 3 | 2.5 | Medium | 52-70 | 51-69 | | |
| 4 | 5 | High | 72-90 | 71-89 | 92-100 | 91-99 |

Table 2 (Satellite Groups):

TABLE 2

| | | | Rat Numbers | |
|---|---|---|---|---|
| Group Number | Dosage (mg/kg/day) | Treatment/ Level | M (even) | F (odd) |
| 5 | 0 | Control | 102-106 | 101-105 |
| 6 | 0.5 | Low | 108-124 | 107-123 |
| 7 | 2.5 | Medium | 126-142 | 125-141 |
| 8 | 5 | High | 144-160 | 143-159 |

The treatment sites were examined each day, approximately 3 hours after the start of dosing. Irritation of the sites, when compared to the adjacent untreated skin, was assigned a numerical value according to the table below:

| | Value |
|---|---|
| Erythema and eschar formation | |
| No erythema | 0 |
| Very slight erythema (barely perceptible) | 1 |
| Well defined erythema | 2 |
| Moderate to severe erythema | 3 |
| Severe erythema (beet redness) to eschar formation preventing grading of erythema | 4 |
| Oedema formation | |
| No oedema | 0 |
| Very slight oedema (barely perceptible) | 1 |
| Slight oedema (edges of area well defined by definite raising) | 2 |
| Moderate oedema (raised approximately one millimetre) | 3 |
| Severe oedema (raised more than one millimetre and extending beyond the area of exposure) | 4 |

Results

No treatment-related mortality occurred during the study (one female from the high-dose group died on Day 40 of the study) and no treatment-related clinical signs were observed. No relevant differences in body weight were recorded and food consumption of treated animals remained comparable to controls throughout the study.

No signs of irritation were observed at treated sites (irritation index was 0).

No treatment-related lesions were detected at the ophthalmic examination performed at the end of the treatment period.

From an haematological point of view, leucopenia observed in animals of high dose group and in females of medium dose group showed a partial reversibility at the end of the recovery period. No other change of toxicological significance was observed.

No changes of toxicological significance were observed both from clinical chemistry and urinalysis.

Terminal body weight was comparable between control and treated groups.

No changes in absolute and relative organ weights of toxicological significance were observed.

No treatment-related changes were noted after macroscopic and microscopic observations.

For what concern toxicokinetics, on Day 1, plasma levels of test item were generally below the LLOQ (lower limits of quantitation, =49.9 ng/ml) in males and females receiving 0.5, 2.5 and 5 mg/kg/day of the test item, when only individual animals occasionally showed values slightly >LLOQ between 2 and 8 hours post-dose. Measured values were not proportional to the dose level.

Similar results were observed at weeks 4 and 13, when a lower incidence of absorption was detected. This was particularly evident at week 4 in the males, which showed occasional values slightly >LLOQ between 6 and 8 hours post-dose only in animals receiving 5 mg/kg/day of the test item and at week 13 in the females (values slightly >LLOQ between 4 and 8 hours post-dose only at 5 mg/kg/day).

No detectable levels were measured for animals of group treated with the vehicle alone. On the basis of the above results, no accumulation has occurred after daily administration over a 13 week period.

Conclusions

No adverse effects were seen at any of the dose levels of the test item investigated (i.e. 0.5, 2.5 and 5 mg/kg/day). The slight leucopenia observed in the treated animals when compared to controls, was not considered of toxicological importance as it was of low magnitude, generally not dose-related and not supported by any microscopic changes. Therefore, the high-dose of 5 mg/kg/day is considered to be the No Observed Adverse Effect Level (NOAEL) for the test item after daily dermal administration to rats over a period of 13 weeks.

Results of plasma sample analyses showed that the test item is only minimally absorbed though the dermal route.

Example 9

13 Week Dermal Toxicity Study in Rabbits Followed by a 4 Week Recovery Period

The toxicity of the test item was investigated in rabbits after daily dermal administration at dose levels of 0.5, 2.5 and 5 mg/animal/day over a period of 13 weeks and recovery from any potential treatment-related effects over a period of 4 consecutive weeks.

Three groups, each of 6 male and 6 female New Zealand White Specific Pathogen Free (SPF) rabbits (cf. Table 3: male numbered with even numbers, female numbered with uneven numbers), received the test item by dermal application at dosages of 0.5, 2.5 and 5 mg/animal/day for 13 consecutive weeks (Table 3, group numbers 2-4, respectively). A fourth similarly constituted group received the vehicle alone (purified water) and acted as a control (Table 3, group number 1). Control and high dose groups (Table 3, group numbers 4 and 1, respectively). included 3 additional animals per sex for recovery assessment.

The group identification and treatment are summarised in Table 3 below:

TABLE 3

| | | | Rabbit numbers | | | |
|---|---|---|---|---|---|---|
| | | | Main phase | | Recovery phase | |
| Group Number | Treatment (mg/animal/day) | Level | M (even) | F (odd) | M (even) | F (odd) |
| 1 | 0 | Control | 2-12 | 1-11 | 14-18 | 13-17 |
| 2 | 0.5 | Low | 20-30 | 19-29 | | |
| 3 | 2.5 | Medium | 32-42 | 31-41 | | |
| 4 | 5 | High | 44-54 | 43-53 | 56-60 | 55-59 |

The following investigations were performed: daily clinical signs, body weight, food consumption, macroscopic observations of the treatment sites, clinical pathology investigations, terminal body weight, organ weight, post mortem macroscopic observations and histopathological examination.

Blood samples were taken from each animal on Day 1 and Week 13 for toxicokinetic evaluations.

The treatment sites were examined, each day, approximately 3 hours after the start of dosing. Irritation of the sites, when compared to the adjacent untreated skin, was assigned a numerical value according to the table below:

| | Value |
|---|---|
| Erythema and eschar formation | |
| No erythema | 0 |
| Very slight erythema (barely perceptible) | 1 |
| Well defined erythema | 2 |
| Moderate to severe erythema | 3 |
| Severe erythema (beet redness) to eschar formation preventing grading of erythema | 4 |
| Oedema formation | |
| No oedema | 0 |
| Very slight oedema (barely perceptible) | 1 |
| Slight oedema (edges of area well defined by definite raising) | 2 |
| Moderate oedema (raised approximately one millimetre) | 3 |
| Severe oedema (raised more than one millimetre and extending beyond the area of exposure) | 4 |

Results

No treatment-related mortality occurred during the study (one male from the recovery control group was humanely killed on Day 29 of the study) and no treatment-related clinical signs were observed.

No signs of irritation were observed after macroscopic observations of treated sites.

No relevant differences in body weight were recorded during the study and food consumption of treated animals remained comparable to controls.

At the ophthalmic examination performed at the end of the treatment period, no treatment-related lesions were detected For haematology and clinical chemistry, no changes of toxicological significance were recorded.

For what concern toxicokinetics, at week 1, plasma levels of the test item were slightly >LLOQ (lower limit of quantitation, =51.30 ng/ml) in the majority of males receiving 2.5 mg/kg/day of the test item and in females receiving 5 mg/kg/day. Only individual male animals dosed at 0.5 and 5 mg/kg/ day occasionally showed values slightly >LLOQ. The incidence of absorption was slightly higher in males compared to females. Absorption was not proportional to the dose level.

Very low absorption was also observed at week 13. Values >LLOQ were generally reported between 2 and 24 hours post-dose. The absorption was slightly higher in females than in males.

No detectable levels were measured for animals treated with the vehicle alone.

On the basis of the above results, no accumulation occurred after daily administration over a 13 week period.

Terminal body weight was comparable between control and treated groups and no changes in absolute and relative organ weight of toxicological significance were observed.

After macroscopic and microscopic observations no treatment-related changes were noted.

Conclusions

No adverse effects were seen at any of the dose levels of the test item investigated (i.e. 0.5, 2.5 and 5 mg/animal/day). Therefore, the high-dose of 5 mg/animal/day is considered to be the No Observed Adverse Effect Level (NOAEL) for the test item after daily dermal administration to rabbits over a period of 13 weeks.

Results of plasma sample analyses showed that the test item is only minimally absorbed through the dermal route.

Example 10

Acute Intravenous Toxicity Study in Rats

The acute toxicity of the conjugate of Example 3 was investigated after intravenous administration (10 ml/kg in physiological saline) of a single dose to Sprague Dawley rats followed by a 14-day observation period.

A single group of 5 male and 5 female animals was dosed at 2000 mg/kg. Animals were dosed with the formulated test item at the selected level, just after its preparation, by injection into the tail vein using a hypodermic needle attached to a syringe of suitable capacity, at a dose volume of 10 ml/kg body weight. Throughout the study, all animals were checked twice daily.

Animals were examined for signs of reaction to treatment on dosing, approximately 30 min, 2 and 4 hours after dosing on day 1, then daily for a total of 14 days. Each animal was weighed on the day of allocation to study, on the day of dosing (day 1) and on days 2, 8 and 15. All animals were killed at the end of the observation period and subjected to necropsy examination.

No mortality occurred in both male and female animals. The clinical sign observed in all animals on the day of dosing were reduced activity and piloerection. In a single female was noted hairloss on the dorsum during the second week of the study.

Changes in body weight observed at the end of the study were within the expected range for this strain and age of animals. No internal abnormalities were detected in any animals at the necropsy examination. No abnormalities were observed at the injection site.

These results indicate that the conjugate had no toxic effect on the rat following a single intravenous administration at a dose level of 2000 mg/kg body weight. Only minor clinical signs were observed in the animals. The test item was locally tolerated when injected into the tail vein at the dose level tested.

Example 11

Mutation in L5178Y TK$^{+/-}$ Mouse Lymphoma Cells
(Fluctuation Method)

The test item was examined for mutagenic activity by assaying for the induction of 5-trifluorothymidine resistant mutants in mouse lymphoma L5178Y cells after in vitro treatment, in the absence and presence of S9 metabolic activation, using a fluctuation method. This method may detect gene mutation, clastogenic and aneugenic effects.

The mutation assay method used in this study is based on the identification of L5178Y colonies which have become resistant to a toxic thymidine analogue trifluorothymidine (TFT). This analogue can be metabolised by the enzyme thymidine kinase (TK) into nucleosides, which are used in nucleic acid synthesis resulting in the death of TK-competent cells.

TK-deficient cells, which are presumed to arise through mutations in the TK gene, cannot metabolise trifluorothymidine and thus survive and grow in its presence.

In the L5178Y mouse lymphoma cells, the gene which codes for the TK enzyme is located on chromosome 11. Cells which are heterozygous at the TK locus (TK+/−) may undergo a single step forward mutation to the TK−/− genotype in which little or no TK activity remains.

The cells used, L5178Y TK+/−, are derived from one of the two clones originated from a thymic tumour induced in a DBA/2 mouse by methylcholanthrene. The use of the TK mutation system in L5178Y mouse lymphoma cells has been well characterised and validated (Clive D, Johnson K O, Spector J F, Batson A G, Brown M M. Validation and characterization of the L5178Y/TK+/− mouse lymphoma mutagen assay system. Mutat Res. 1979 January; 59(1):61-108.) and is accepted by most of the regulatory authorities.

The mouse lymphoma assay often produces a bimodal size distribution of TFT resistant colonies designated as small or large. It has been evaluated that point mutations and deletions within the active allele (intragenic event) produce large colonies. Small colonies result in part from lesions that affect not only the active TK allele but also a flanking gene whose expression modulates the growth rate of cells.

The test item was found to be soluble in RPMI 1640 complete medium at the concentration of 50.0 mg/ml.

A preliminary cytotoxicity assay was performed. Based on the solubility results, the test item was assayed at a maximum dose level of 5000 µg/ml both in the absence and presence of S9 metabolism. A wide range of lower dose levels were included in the treatment series: 2500, 1250, 625, 313, 156, 78.1, 39.1 and 19.5 µg/ml.

In the absence of S9 metabolic activation, using the short treatment time, slight reduction of relative survival was noted at several concentrations without a dose relationship. Using the long treatment time, toxicity was observed at the two higher concentrations reducing the relative survival at approximately 60% of the concurrent negative control value.

In the presence of S9 metabolic activation, no relevant toxicity was observed at any concentration tested.

Based on the toxicity results obtained in the preliminary trial, two independent assays for mutation to 5-trifluorothymidine resistance were performed using the dose levels described in the following table 4:

TABLE 4

| Assay No.: | S9 | Treatment Time (hours) | Dose level (µg/ml) |
|---|---|---|---|
| 1 | −/+ | 3 | 5000, 2500, 1250, 625 and 313 |
| 2 | − | 24 | 5000, 2500, 1250, 625 and 313 |
| 2 | + | 3 | 5000, 3571, 2551, 1822 and 1302 |

No relevant increases in mutant frequencies were observed following treatment with the test item, in the absence or presence of S9 metabolism.

Solvent and positive control treatments were included in each mutation experiment in the absence and presence of S9 metabolism. The mutant frequencies in the solvent control cultures fell within the normal range. Marked increases were obtained with the positive control treatments indicating the correct functioning of the assay system.

It is concluded that the test item does not induce mutation in mouse lymphoma L5178Y cells after in vitro treatment in the absence or presence of S9 metabolic activation, under the reported experimental conditions.

Example 12

Photomutagenicity Assay in Bacteria (*S. typhimurium* and *E. coli*)

The test item was examined for photomutagenic activity by assaying for reverse mutation to prototrophy in the prokaryotic organisms, *Salmonella typhimurium* and *Escherichia coli*, after exposure to light.

The three *S. typhimurium* tester strains, TA1537, TA98 and TA100, and the *E. coli* tester strain, WP2, were used. The bacteria, co-plated with the test item in soft-agar, were irradiated with various doses of UV light.

The procedures adopted were developed by Ames et al., 1975 and revised by Maron and Ames, 1983.

The test item was used as a solution in sterile distilled water.

The test item was assayed in the toxicity test at a maximum dose level of 5000 µg/plate and at four lower concentrations spaced at approximately half-log intervals: 1580, 500, 158 and 50.0 µg/plate. Two widely-spaced UV doses were selected for each bacterial tester strain on the basis of the maximum tolerated dose. No relevant toxicity was observed at any concentration of the test item or at any UV irradiation dose.

Two independent experiments were performed using the plate incorporation method.

The test item was assayed at a maximum dose level of 5000 µg/plate and at four lower dose levels spaced by two-fold dilutions: 2500, 1250, 625 and 313 µg/plate. The prepared plates were exposed to the following UVA and UVB doses (Table 5):

TABLE 5

| Tester strain | UVA (J/cm$^2$) | UVB (J/cm$^2$) |
|---|---|---|
| TA1537 | 0.4 | — |
|  | 0.2 | — |
|  | 0.1 | — |
| TA98 | 0.2 | — |
|  | 0.1 | — |
|  | 0.05 | — |
| TA100 | 0.04 | — |
|  | 0.02 | — |
|  | 0.01 | — |
| WP2 | 0.004 | 0.004 |
|  | 0.002 | 0.002 |
|  | 0.001 | 0.001 |

Results

The test item did not induce two-fold increases in the number of revertant colonies over the background UV effect at any dose level of the test item, in any tester strain, at any UV irradiation dose.

Conclusions

It is concluded that the test item does not induce reverse mutation in *Salmonella typhimurium* or *Escherichia coli*, when treatment was performed in the presence of UV light.

Example 13

Chromosome Aberrations in Chinese Hamster Ovary Cells In Vitro (Photomutagenicity Assay)

The test item was assayed for the ability to cause chromosomal damage in Chinese hamster ovary cells, following in vitro treatment in the absence and presence of UVA/UVB irradiation.

One assay for chromosomal damage was performed at dose levels of 5000, 2500, 1250, 625, 313, 156, 78.1 and 39.1 µg/ml both in the absence and presence of ultraviolet light were employed in the assay.

Solutions of the test item were prepared in Hank's Balanced Salt Solution (HBSS).

Both in the absence and presence of UV light, the cells were treated for 3 hours and the harvest time of 20 hours, corresponding to approximately 1.5 cell cycle, was used.

The experiment included appropriate negative and positive controls. Two cell cultures were prepared at each test point.

Dose levels were selected for the scoring of chromosomal aberrations on the basis of the cytotoxicity of the test item treatments as determined by the reduction of cell counts at the time of harvesting.

Since no remarkable toxicity was observed over the whole dose range, the dose levels selected for scoring were 5000, 2500 and 1250 µg/ml both in the absence and presence of UV light.

One hundred metaphase spreads were scored for chromosomal aberrations from each culture.

Results

Following treatment with the test item, no statistically significant increase in the incidence of cells bearing aberrations, including or excluding gaps, compared with the relevant control values, was observed in the absence or presence of ultraviolet light.

Statistically significant increases in the number of cells bearing aberrations (including and excluding gaps) were observed following treatments with the positive controls Mitomycin-C and 8-Methoxypsoralen indicating the correct functioning of the test system.

Conclusions

On the basis of these results it is concluded that, under the reported experimental conditions, the test item does not induce chromosomal aberrations in Chinese hamster ovary cells after in vitro treatment in the absence or presence of UV light.

Example 14

Balb/C 3t3 Cell Phototoxicity Assay (Neutral Red Uptake)

The potential in vitro phototoxicity of the test item was evaluated by the measurements of neutral red uptake for cellular toxicity on cultures of Balb/c 3T3 cells treated with different doses of the test item and exposed to UVA irradiation. Test item solutions were prepared using Earle's Balanced Salt Solution (EBSS).

A preliminary dose-range finding experiment in the presence (+UVA) and in the absence (−UVA) of light was undertaken in order to select appropriate dose levels for the main assays. The test item was assayed at a maximum dose level of 1000 µg/ml (the upper limit indicated in the study protocol) and at a wide range of lower dose levels: 500, 250, 125, 62.5, 31.3, 15.6 and 7.81 µg/ml. Since no $IC_{50}$ value was calculable both in the presence and in the absence of UVA irradiation, also the Photo Irritation Factor (PIF) value could not be calculated. In this case the chemical is considered to be non-phototoxic. The same dose range was used for the main assay.

A main experiment was performed using the following dose levels: 1000, 500, 250, 125, 62.5, 31.3, 15.6 and 7.81 µg/ml. The survival curves in the presence and in the absence of UV light showed a similar profile, confirming the results obtained in the preliminary dose-range finding experiment. The Photo Irritation Factor (PIF) value could not be calculated since there was no $IC_{50}$ value for both curves. The mean photo effect (MPE) was 0.089 which falls within the non phototoxic range.

Since this experiment produced clearly negative results, no further experiments were undertaken.

The positive control Chlorpromazine induced an acceptable positive response with a PIF value of 21.9 indicating the correct functioning of the assay system.

Since a no-calculable PIF or a MPE<0.1 predicts "no phototoxicity", on the basis of the results obtained, it is concluded that the test item should be classified as "non phototoxic" under the reported experimental conditions.

Example 15

Test Item 0.1% Cream Photoirritation/Photosensitisation Study in Guinea Pigs The potential of the test item 0.1% cream to cause photoallergic and/or photoirritant reactions following topical application to the skin, in association with exposure to ultraviolet light, was assessed using a guinea pig model.

The study was divided into 2 phases.

In the first phase, an assessment of the photoirritant properties of the test item was performed in 6 groups of animals. These were used both to establish suitable concentrations of the test item for use in the sensitisation assay and to provide information on photo-induced irritation. Animals were treated as follows (Table 6):

TABLE 6

| Group number | Treatment | UV irradiation | Number of animals |
|---|---|---|---|
| 1 | Vehicle + Control item | Yes | 5 |
| 2 | Vehicle + Control item | No | 5 |
| 3 | Vehicle + Test item | Yes | 5 |

TABLE 6-continued

| Group number | Treatment | UV irradiation | Number of animals |
|---|---|---|---|
| 4 | Vehicle + Test item | No | 5 |
| 5 | Vehicle + 8-methoxypsoralen | No | 5 |
| 6 | Vehicle + 8-methoxypsoralen | Yes | 5 |

The second phase of the study was an assessment of sensitisation, in which a total of 5 groups were treated as follows (Table 7):

TABLE 7

| Group number | Treatment at induction | Treatment at challenge | Number of animals |
|---|---|---|---|
| 7 | F.C.A.[1] + Vehicle | | 10 |
| | | Vehicle + Test item | 5 of the 10 |
| | | Vehicle + Control item | 5 of the 10 |
| 8 | F.C.A. + Control item | Vehicle Control item | 10 |
| 9 | F.C.A. + Test item | Vehicle Test item | 10 |
| 10 | F.C.A. + Vehicle | Vehicle Musk Ambrette | 3 |
| 11 | F.C.A. + Musk Ambrette | Vehicle Musk Ambrette | 5 |

[1]Freund's Complete Adjuvant

Photoirritation

The photoirritation test was undertaken using 2 (irradiated) groups, each of 5 animals, treated with the control and test items, cream placebo and test item 0.1% cream, respectively (cf. Table 6, groups 1 and 3) and 2 similarly constituted groups (cf. Table 6, groups 2 and 4), treated in the same manner but not irradiated. Aliquots of the undiluted test or control item (100%), 2 concentrations (20% and 50% in purified water) of the test and control items and the vehicle alone (purified water), were spread evenly over defined skin sites prepared on the dorsum of the animals. Animals of the irradiated groups (groups 1 and 3) were exposed to both UVA (10 Joules/cm$^2$) and UVB (0.1 Joules/cm$^2$) radiation following dosing. A positive control reference substance, 8-methoxypsoralen, was investigated using the same methods at concentrations of 0.001%, 0.01% and 0.1%, in 5 test (irradiated) and 5 control (non-irradiated) animals (cf. Table 6, groups 6 and 5, respectively). Approximately 1, 4, 24, 48 and 72 hours after exposure to the control, test or reference items, the treated sites were examined for evidence of an irritant reaction to treatment.

Results

A slight irritation was observed in 1/5 animals at the sites treated with the test item 0.1% cream and UV irradiated. A slight to well defined reaction was observed in 4/5 animals treated with the test item but not UV-irradiated.

A slight reaction was also observed in 1/5 animals treated with the control item (cream placebo) not UV-irradiated.

No reaction was observed at sites treated with the vehicle alone.

The irritant reaction observed in animals treated with the test item was not photo-induced as it was seen in both UV-irradiated and, with higher severity, in not-irradiated animals.

A slight occasional reaction was also observed in not-irradiated animals treated with the control item.

Animals treated with the positive control reference item, 8-methoxypsoralen, and then exposed to ultraviolet light, exhibited a well defined to moderate erythema and a slight oedema at sites treated with the 2 higher concentrations investigated, 0.01% and 0.1%. No response was seen in those animals exposed to 8-methoxypsoralen without subsequent exposure to ultraviolet light, demonstrating that the observed response was photo-induced.

Photosensitisation

The photosensitisation test was undertaken using 2 groups of 10 animals (cf. Table 7, groups 8 and 9) induced with the control item and the test item and 1 control group of 10 animals (cf. Table 7, group 7) induced with the selected vehicle (purified water). In an attempt to induce sensitisation, animals were intradermally injected with an emulsion of Freund's complete adjuvant. The test and control items, at 100% concentration, were applied topically over the area among the injection sites of FCA a total of 6 times over a 2 week period. Animals were exposed to both UVA (10 Joules/cm$^2$) and UVB (0.1 Joules/cm$^2$) radiation following dosing. Control group animals were treated in the same manner but the selected vehicle (purified water) was used in place of the test or control items. Approximately 2 weeks after the final induction exposure, all animals were challenged by topical application of both the vehicle and the test or control item at 20% and 50% concentrations, respectively. These concentrations were selected as they were considered non-irritant to the skin in association with ultraviolet irradiation on the basis of the results obtained at the photoirritation test. Animals of the 2 test groups and the control group were exposed to both UVA (10 Joules/cm$^2$) and UVB (0.1 Joule/cm$^2$) radiation following dosing. Additional sites on each animal were topically treated with both the vehicle and test or control items, but treatment was not followed by exposure to ultraviolet irradiation. Approximately 24, 48 and 72 hours after challenge exposure the treated sites were examined for evidence of reaction to treatment.

A positive control reference item, Musk Ambrette, was investigated using the same methods to prove the validity of the test system. One group of 5 animals (cf. Table 7, group 11) was induced with this substance at a concentration of 15% in acetone. A control group of 3 animals (cf. Table 7, group 10) was treated in the same manner with the vehicle alone (acetone). A concentration of 10% of the reference item (Musk Ambrette) in acetone was selected for the challenge.

Results

Challenge with the control item, cream placebo, at 50% concentration followed by ultraviolet irradiation resulted in response to the control item in 10/10 animals of the group (group 8). Response to the control item was observed in 6/10 animals of group 8 at sites treated but not irradiated. Reaction was also observed in 5/5 control group animals (group 7) at sites treated at challenge with the control item followed by ultraviolet irradiation and in 4/5 control animals at sites treated with the control item but not irradiated. No reaction to the vehicle alone was observed.

Challenge with the test item 0.1% cream at 20% concentration followed by ultraviolet irradiation resulted in response to the test item in 8/10 animals of the group (group 9). No response to the test item was observed in animals of group 9 at sites treated but not irradiated. Reaction was also observed in 5/5 control group animals (group 7) at sites treated at challenge with the test item followed by ultraviolet irradiation and in 1/5 control animal at sites treated with the test item but not irradiated. No reaction to the vehicle alone was observed.

On the basis of the above results, a response was observed in animals treated either with the test or control item. The reaction, being observed in control group animals (not induced with the test item), was due to an irritant effect of the substance rather than to sensitisation. In addition, the reaction was observed also at sites not UV-irradiated.

As a result, a second challenge (re-challenge) was performed with the test and control items at a lower concentration of 5%.

No response was observed in any animal of groups 8 and 9 at re-challenge with the test and control items at 5% concentration, followed by ultraviolet irradiation. No response to the test or control items was observed in animals of groups 8 or 9 at sites treated but not irradiated. No reaction at any sites was observed in control group animals (group 7) treated at challenge with the control or test items. No reaction to the vehicle alone was seen.

Challenge of positive control animals with the reference item (Musk Ambrette) at 10% concentration followed by ultraviolet irradiation produced a response (very slight to slight erythema) in 4/5 animals of the group (group 11). No response to the reference item was observed in animals of group 11 at sites treated but not irradiated. No response to the reference item was observed in animals of group 10, induced with the vehicle. This indicates the test system to be capable of detecting the photoallergic properties of substances.

Conclusions

The results obtained give no indication that the test item 0.1% cream may cause a photoirritant or photoallergic response following dermal exposure in association with ultraviolet light.

The invention claimed is:
1. A process for the preparation of a polymer conjugate of an indolocarbazole compound of formula (I)

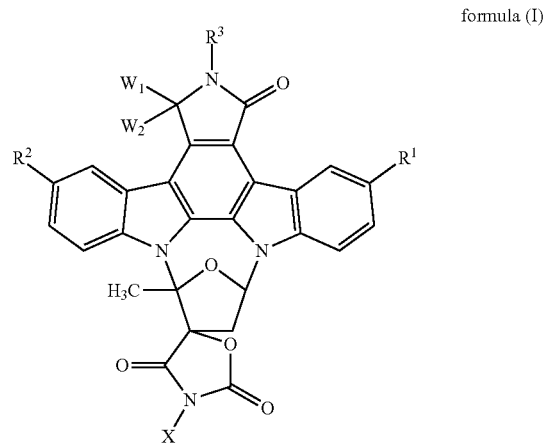

formula (I)

wherein
$R^1$ and $R^2$ are the same or a different residue and are each independently selected from the group consisting of:
(a) hydrogen, halogen, substituted or unsubstituted lower alkyl, substituted or unsubstituted lower alkenyl, substituted or unsubstituted lower alkynyl, hydroxy, lower alkoxy, carboxy, lower alcoxycarbonyl, acyl, nitro, carbamoyl, lower alkylaminocarbonyl, —NR$^5$R$^6$, wherein R$^5$ and R$^6$ are each independently selected from hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, substituted or unsubstituted aralkyl, substituted or unsubstituted lower alkylaminocarbonyl, substituted or unsubstituted lower arylaminocarbonyl, alkoxycarbonyl, carbamoyl, acyl or $R^5$ and $R^6$ are combined with a nitrogen atom to form a heterocyclic group,
(b) —CO(CH$_2$)$_j$R$^4$, wherein j is 1 to 6, and $R^4$ is selected from the group consisting of
  (i) hydrogen, halogen, —N$_3$,
  (ii) —NR$^5$R$^6$, wherein $R^5$ and $R^6$ are as defined above,
  (iii) —SR$^7$, wherein $R^7$ is selected from the group consisting of hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, substituted or unsubstituted aralkyl, —(CH$_2$)$_a$CO$_2$R$^{10}$ (wherein a is 1 or 2, and wherein $R^{10}$ is selected from the group consisting of hydrogen and substituted or unsubstituted lower alkyl) and —(CH$_2$)$_a$CO$_2$NR$^5$R$^6$,
  (iv) —OR$^8$, —OCOR$^8$, wherein R8 is selected from hydrogen, substituted or unsubstituted lower alkyl, substituted or unsubstituted lower alkenyl, substituted or unsubstituted lower alkynyl, substituted or unsubstituted aryl, substituted or unsubstituted heteroaryl
(c) —CH(OH)(CH$_2$)$_j$R$^{4t}$ wherein j and $R^4$ are as defined above;
(d) —(CH$_2$)$_d$CHR$^{11}$CO$_2$R$^{12}$ or —(CH$_2$)$_d$CHR$^{11}$CONR$^5$R$^6$, wherein d is 0 to 5, $R^{11}$ is hydrogen, —CONR$^5$R$^6$, or —CO$_2$R$^{13}$, wherein $R^{13}$ is hydrogen or a wherein substituted or unsubstituted lower alkyl, and $R^{12}$ is hydrogen or a substituted or unsubstituted lower alkyl;
(e) —(CH$_2$)$_k$R$^{14}$ wherein k is 2 to 6 and $R^{14}$ is halogen, substituted or unsubstituted aryl, substituted or unsubstituted heteroaryl, —COOR$^{15}$, —OR$^{15}$, (wherein $R^{15}$ is hydrogen, substituted or unsubstituted lower alkyl, substituted or unsubstituted lower alkenyl, substituted or unsubstituted lower alkynyl, substituted or unsubstituted aryl, substituted or unsubstituted heteroaryl or acyl), —SR$^7$ (wherein $R^7$ is as defined above), —CONR$^5$R$^6$, —NR$^5$R$^6$ (wherein $R^5$ and $R^6$ are as defined above) or —N$_3$;
(f) —CH=CH(CH$_2$)$_m$R$^{16}$, wherein m is 0 to 4, and $R^{16}$ is hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, —COOR$^{15}$, —OR$^{15}$ (wherein $R^{15}$ is as defined above) —CONR$^5$R$^6$ or —NR$^5$R$^6$ (wherein $R^5$ and $R^6$ are as defined above);
(g) —CH=C(CO$_2$R$^{12}$)$_2$, wherein $R^{12}$ is as defined above;
(h) —C≡C(CH$_2$)$_n$R$^{16}$, wherein n is 0 to 4 and $R^{16}$ is as defined above;
(i) —CH$_2$OR$^{22}$, wherein $R^{22}$ is tri-lower alkyl silyl in which the three lower alkyl groups are the same or different or wherein $R^{22}$ has the same meaning as $R^8$
(j) —CH(SR$^{23}$)$_2$ and —CH$_2$—SR$^7$ wherein $R^{23}$ is lower alkyl, lower alkenyl or lower alkynyl and wherein $R^7$ is as defined above; and
$R_3$ is hydrogen, halogen, acyl, carbamoyl, substituted or unsubstituted lower alkyl, substituted or unsubstituted lower alkenyl, substituted or unsubstituted lower alkynyl or amino; and
$W^1$ and $W^2$ are independently hydrogen, hydroxy or $W^1$ and $W^2$ together represent oxygen;
and wherein X is a polymer moiety, whereby the process comprises reacting a ω-1H-imidazole-carboxamide polymer compound of general formula (II)

$$X-NH-C(=O)-N(imidazole)$$ formula (II)

wherein X is defined as above with an indolocarbazole compound of general formula (III)

formula (III)

[indolocarbazole structure with substituents $R_1$, $R_2$, $R_3$, $W_1$, $W_2$, H$_3$C, HO, COY]

wherein $R_1$, $R_2$, $R_3$, $W_1$ and $W_2$ are defined as above and which are optionally protected by protecting groups and wherein Y represents a leaving group and wherein the process further optionally comprises deprotecting the groups $R_1$, $R_2$, $R_3$, $W_1$ and $W_2$ in order to obtain the compound of Formula (I).

2. The process according to claim 1, wherein the process is carried out in the presence of a base in an organic solvent.

3. The process according to claim 2, wherein the molar ratio of the base to the compound of formula (III) is between about 1:1 and about 4:1.

4. The process according to claim 2, wherein the base is selected from the group of alkali metal hydrides.

5. The process according to claim 1, wherein the process is carried out in an organic solvent.

6. The process according to claim 1, wherein the process is carried out under inert gas atmosphere.

7. The process according to claim 1, wherein the process is carried out at a temperature of −10 to 60° C.

8. The process according to any one of the preceding claims, wherein the polymer conjugate compound of formula (I) is directly obtained by chromatographic purification.

9. The process according to claim 8, wherein the purification of the polymer conjugate compound of formula (I) is performed in a solvent.

10. The process according to any one of the preceding claims, wherein the leaving group Y is selected from a triflate, a tosylate, a mesylate, a sulfate, a halogen, a hydroxy or a lower alkoxy group.

11. The process according to claim 1, wherein the leaving group Y is a lower alkoxy group.

12. The process according to claim 1, wherein the polymer X is selected from poly(alkylene oxides).

13. The process according to claim 12, wherein the polymer X is a (polyethylene) glycol (PEG).

14. The process according to claim 1, wherein the polymer X has a molecular weight from about 100 to about 100,000 Da.

15. The process according to claim 13, wherein the polymer X is a (polyethylene) glycol with an average molecular weight of about 500 to about 10000 Da.

16. The process according to anyone of the preceding claims, wherein $R_1$, $R_2$, $R_3$, $W_1$ and $W_2$ are hydrogen.

17. A polymer conjugate of an indolocarbazole compound of formula (I)

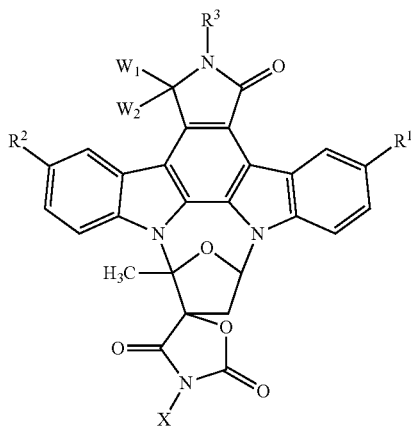

formula (I)

wherein
$R_1$, $R_2$, $R_3$, $W_1$, $W_2$ and X are as defined in claim 1;
or a pharmaceutically acceptable salt thereof.

18. Polymer conjugate according to claim 17, wherein $R_1$, $R_2$, $R_3$, $W_1$ and $W_2$ are hydrogen.

19. Polymer conjugate according to claim 17, wherein the polymer X is a (polyethylene) glycol, with an average molecular weight of about 500 to about 10,000 Da.

20. Polymer conjugate according to any one of claims 17 to 19 for use in a medicament.

21. Polymer conjugate according to claim 20 for use in a medicament for topical applications.

22. Polymer conjugate according to claim 20 for use as in a medicament for systemic applications.

23. Pharmaceutical composition comprising at least one polymer conjugate of any one of claims 17 to 19, optionally together with pharmaceutically acceptable carriers, adjuvants, diluents or/and additives.

24. Pharmaceutical composition according to claim 23 for diagnostic or/and therapeutic application.

25. The process of claim 3, wherein the molar ratio of the base to the compound of formula (III) is between about 1:1 to about 1.5:1.

26. The process of claim 25, wherein the molar ratio of the base to the compound of formula (III) is about 1:1.

27. The process of claim 4, wherein the base is sodium hydride.

28. The process of claim 5, wherein the process is carried out in an anhydrous organic solvent selected from the group consisting of dichloromethane, chloroform and N,N-dimethylformamide.

29. The process of claim 6, wherein said inert gas atmosphere is a nitrogen or argon atmosphere.

30. The process of claim 7, wherein the process is carried out at a temperature of about 15° to about 25° C.

31. The process of claim 7, wherein the process is carried out at room temperature after an initial step at 0° C.

32. The process of claim 9, wherein said solvent is dichloromethane, water, methanol, acetonitrile, or ammonium formate buffer solution.

33. The process of claim 11, wherein said lower alkoxy group is a methoxy group.

34. The process of claim 1, wherein said polymer X is selected from (polyethylene) oxides.

35. The process of claim 13, wherein said PEG is selected from terminally alkoxy-substituted polyethylene glycols.

36. The process of claim 14, wherein the polymer X has a molecular weight from about 200 to about 50,000 Da.

37. The process of claim 35, wherein said alkoxy-substituted polyethylene glycol is methoxy-polyethylene glycol (m-PEG).

* * * * *